(12) United States Patent
Liu et al.

(10) Patent No.: US 11,042,982 B2
(45) Date of Patent: Jun. 22, 2021

(54) ULTRA-DENSE ELECTRODE-BASED BRAIN IMAGING SYSTEM

(71) Applicant: THE REGENTS OF THE UNIVERSITY OF CALIFORNIA, Oakland, CA (US)

(72) Inventors: Wentai Liu, Los Angeles, CA (US); Ying Li, Los Angeles, CA (US); Jing Qin, Bozeman, MT (US); Chi-Wei Chang, Los Angeles, CA (US); Yi-Kai Lo, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 531 days.

(21) Appl. No.: 15/912,262

(22) Filed: Mar. 5, 2018

(65) Prior Publication Data

US 2018/0276822 A1  Sep. 27, 2018

Related U.S. Application Data

(63) Continuation of application No. PCT/US2016/050452, filed on Sep. 6, 2016.

(60) Provisional application No. 62/215,154, filed on Sep. 7, 2015, provisional application No. 62/308,159, filed on Mar. 14, 2016.

(51) Int. Cl.
*G06T 7/00* (2017.01)
*A61B 5/291* (2021.01)
(Continued)

(52) U.S. Cl.
CPC .......... *G06T 7/0016* (2013.01); *A61B 5/0006* (2013.01); *A61B 5/291* (2021.01);
(Continued)

(58) Field of Classification Search
None
See application file for complete search history.

(56) References Cited

U.S. PATENT DOCUMENTS

2009/0182220 A1   7/2009   Blunt
2010/0322497 A1   12/2010  Dempsey
(Continued)

FOREIGN PATENT DOCUMENTS

CN   102804207 A   11/2012
CN   103181762 A   7/2013
(Continued)

OTHER PUBLICATIONS

European Patent Office (EPO), supplementary European search report dated Jul. 19, 2019, related European patent application No. EP 16844941.1, pp. 1-9, claims searched, pp. 10-16.
(Continued)

*Primary Examiner* — Vikkram Bali
(74) *Attorney, Agent, or Firm* — O'Banion & Ritchey LLP; John P. O'Banion

(57) ABSTRACT

An ultra-dense electrode-based brain imaging system with high spatial and temporal resolution. A Sparsity and Smoothness enhanced Method Of Optimized electrical TomograpHy (s-SMOOTH) based reconstruction technique to improve the spatial resolution and localization accuracy of reconstructed brain images is described. Also described is a graph Fractional-Order Total Variation (gFOTV) based reconstruction technique to improve the spatial resolution and localization accuracy of reconstructed brain images.

38 Claims, 3 Drawing Sheets

Figure 1:
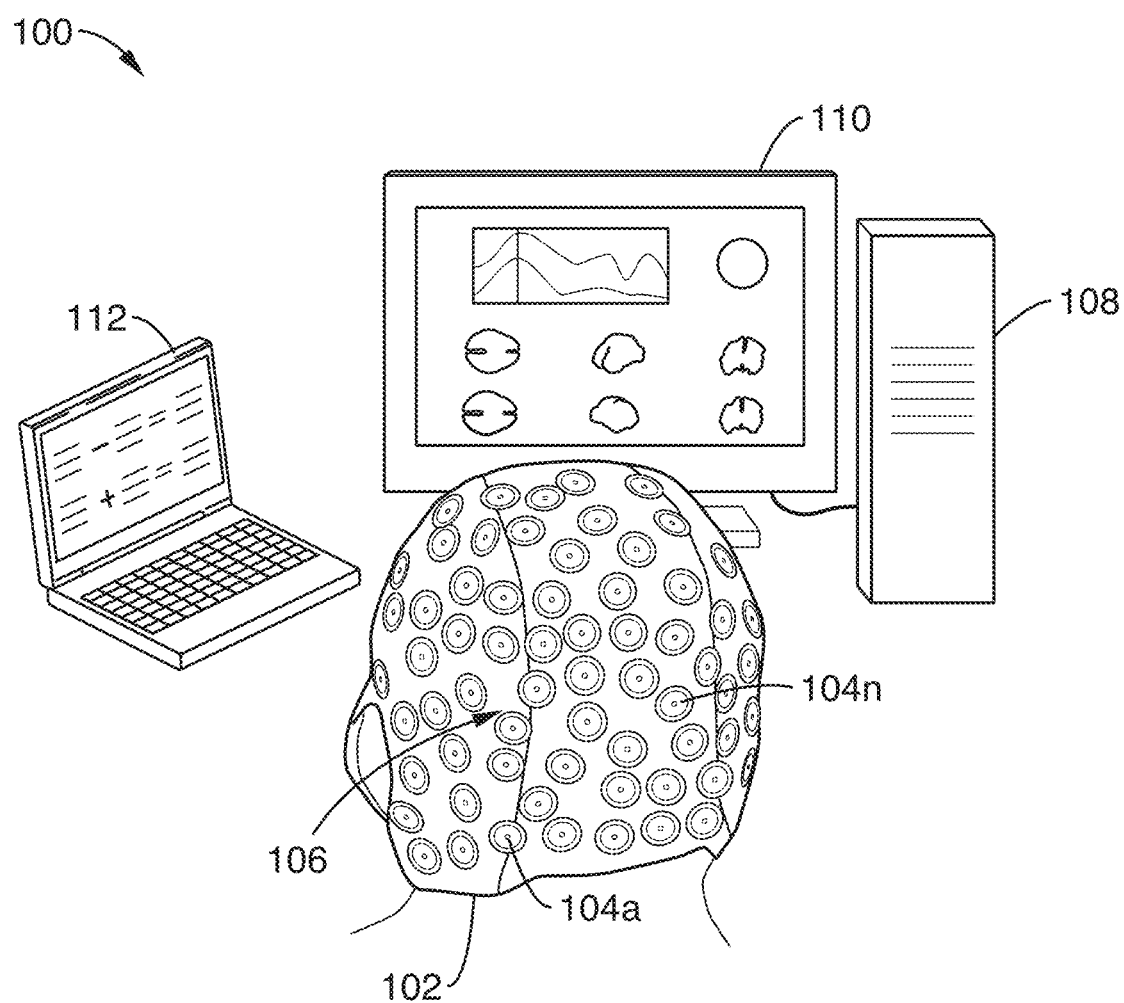

(51) Int. Cl.
*A61B 5/316* (2021.01)
*A61B 5/374* (2021.01)
*A61B 5/378* (2021.01)
*G06T 7/246* (2017.01)
*A61B 5/00* (2006.01)
*G06T 11/00* (2006.01)
*G06T 15/08* (2011.01)
*A61B 5/055* (2006.01)

(52) U.S. Cl.
CPC .............. *A61B 5/316* (2021.01); *A61B 5/374* (2021.01); *A61B 5/378* (2021.01); *A61B 5/721* (2013.01); *A61B 5/743* (2013.01); *G06T 7/248* (2017.01); *G06T 11/005* (2013.01); *G06T 15/08* (2013.01); *A61B 5/055* (2013.01); *G06T 2207/10012* (2013.01); *G06T 2207/10088* (2013.01); *G06T 2207/30016* (2013.01)

(56) References Cited

U.S. PATENT DOCUMENTS

2013/0172718 A1 7/2013 Choi
2013/0204122 A1* 8/2013 Hendler ............... A61B 5/0476
                                              600/411
2014/0012061 A1 1/2014 Song
2015/0038804 A1 2/2015 Younes
2016/0143541 A1* 5/2016 He ....................... A61B 5/6803
                                              600/409

FOREIGN PATENT DOCUMENTS

EP      2591720 A1    5/2013
WO   2009076677 A1    6/2009
WO   2011088227 A1    7/2011
WO   2015009877 A1    1/2015

OTHER PUBLICATIONS

ISA/KR, Korean Intellectual Property Office (KIPO), International Search Report and Written Opinion dated Dec. 22, 2016, PCT international application No. PCT/US2016/050452, pp. 1-13, with claims searched, pp. 14-22.
State Intellectual Property Office of the People's Republic of China (SIPO), official action dated Apr. 10, 2020 (The First Office Action), related Chinese patent application No. 201680051697.2, pp. 1-6, English-language translation, pp. 7-12, claims examined, pp. 13-21.

* cited by examiner

ULTRA-DENSE ELECTRODE-BASED BRAIN IMAGING SYSTEM

CROSS-REFERENCE TO RELATED APPLICATIONS

This application is a 35 U.S.C. § 111(a) continuation of PCT international application number PCT/US2016/050452 filed on Sep. 6, 2016, incorporated herein by reference in its entirety, which claims priority to, and the benefit of, U.S. provisional patent application Ser. No. 62/215,154 filed on Sep. 7, 2015, incorporated herein by reference in its entirety, and which claims priority to, and the benefit of, U.S. provisional patent application Ser. No. 62/308,159 filed on Mar. 14, 2016, incorporated herein by reference in its entirety. Priority is claimed to each of the foregoing applications.

The above-referenced PCT international application was published as PCT International Publication No. WO 2017/044433 on Mar. 16, 2017, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to EEG source imaging, and more particularly to reconstructing brain images with high temporal and spatial resolution.

2. Background Discussion

During the past two decades, electrode systems with 64 to 256 electrodes (electrode pitch at approximately 2 cm) have been adopted in scientific research and clinics. Recently, ultra-dense electrode systems (electrode separation between approximately 3 mm and 10 mm) have become more appreciated in improving brain imaging accuracy since increasing the number of electrodes will improve the spatial resolution in brain imaging. So far, however, researchers have only tried to use small dense arrays (e.g., less than 64 electrodes) to demonstrate the applications of ultra-dense electrode. Unfortunately, an ultra-dense electrode array at a very large size that is able to cover a large portion of the whole head has not yet been developed.

There are several technical challenges associated with implementing a large-size ultra-dense electrode array system. In addition to increasing the number of electrodes, a more advanced inverse algorithm is required in order to significantly improve spatial resolution of the brain image. Total variation (TV) based methods have been proposed which utilize the sparsity property of the brain image in the first spatial derivative rather than in the original source domain. TV-based methods reduce the over-focusing effects of the $l_0$-norm or the $l_1$-norm regularization methods and are able to reconstruct extent of the sources. However, TV-based methods assume the source current density is piece-wise constant, i.e., uniform/constant in each sub-region, which is not realistic in practical applications because the source usually has varying intensities. Consequently this leads to relatively low localization accuracy.

While fMRI is a popular imaging modality since it offers high spatial resolution, its temporal resolution is limited (~1 s), and is inappropriate to be used in portable applications. Thus the capability to meet the need of measuring and manipulating the activity of large ensembles of neurons distributed across anatomically or functionally connected circuits for unrestrained free moving subjects is highly desirable.

BRIEF SUMMARY

This disclosure describes an ultra-dense electrode-based brain imaging system with high spatial and temporal resolution.

In one embodiment, an ultra-dense electrode-based brain imaging system may be implemented as a hardware and software system comprising one or more of the following elements: (1) an ultra-dense electrode array, which is able to fully capture functional brain information; (2) spatially focused techniques, resulting in spatially-focused sensing for forward problem analysis; (3) data acquisition architecture with a gigabit wireless transceiver (TX), that is able to support gigabit bandwidth; (4) a realistic head model, constructed from high-resolution MRI; (5) improved brain imaging reconstruction algorithms, which are able to provide brain dynamics with high spatial resolution and localization accuracy; and (6) integrated software and applications, supporting functions such as hardware manipulation, signal recording and processing, and real-time brain state monitoring. Such an imaging system has wide applications varying from exploring the dynamics of human brain (i.e., memory, behavior, etc.) to diagnosis and treatment of brain disorders (i.e., epilepsy, depression, etc.) as well as to personalized learning.

In one embodiment, the system employs a Sparsity and Smoothness enhanced Method Of Optimized electrical TomograpHy (s-SMOOTH) to improve the spatial resolution and localization accuracy of reconstructed brain images. The method defines a voxel-based Total Generalized Variation (vTGV) regularization on a triangular mesh to enhance high-order smoothness, thus improving the localization accuracy, and utilize $l_{1-2}$ regularization to enhance sparsity of the image thus improving the spatial resolution. A large variety of experiments on synthetic data with different source configurations and noise levels demonstrated the advantages of this method over state-of-the-art in terms of total reconstruction accuracy, localization accuracy and focalization degree. The tests on event-related potential data further demonstrated the outstanding performance of the method in real scenario. This EEG source imaging method may significantly improve the spatial resolution and localization accuracy for brain image reconstruction, and the method shows the potential of developing new applications that require imaging modality for high temporal and spatial resolution with portable mobility.

In another embodiment, the system employs a graph Fractional-Order Total Variation (gFOTV) based method to improve the spatial resolution and localization accuracy of reconstructed brain images. The method provides the freedom to choose the smoothness order by imposing sparsity of the spatial fractional derivatives so that it locates source peaks accurately. We compared the performance of gFOTV and various state-of-the-art methods using a large amount of realistic simulations, and evaluated their relative performances with several quantitative criteria. The results demonstrated the superior performance of gFOTV, not only in high spatial resolution but also in high localization accuracy and total reconstruction accuracy.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 1: Schematic of a brain imaging system according to an embodiment of the technology described herein.

Figure 2:
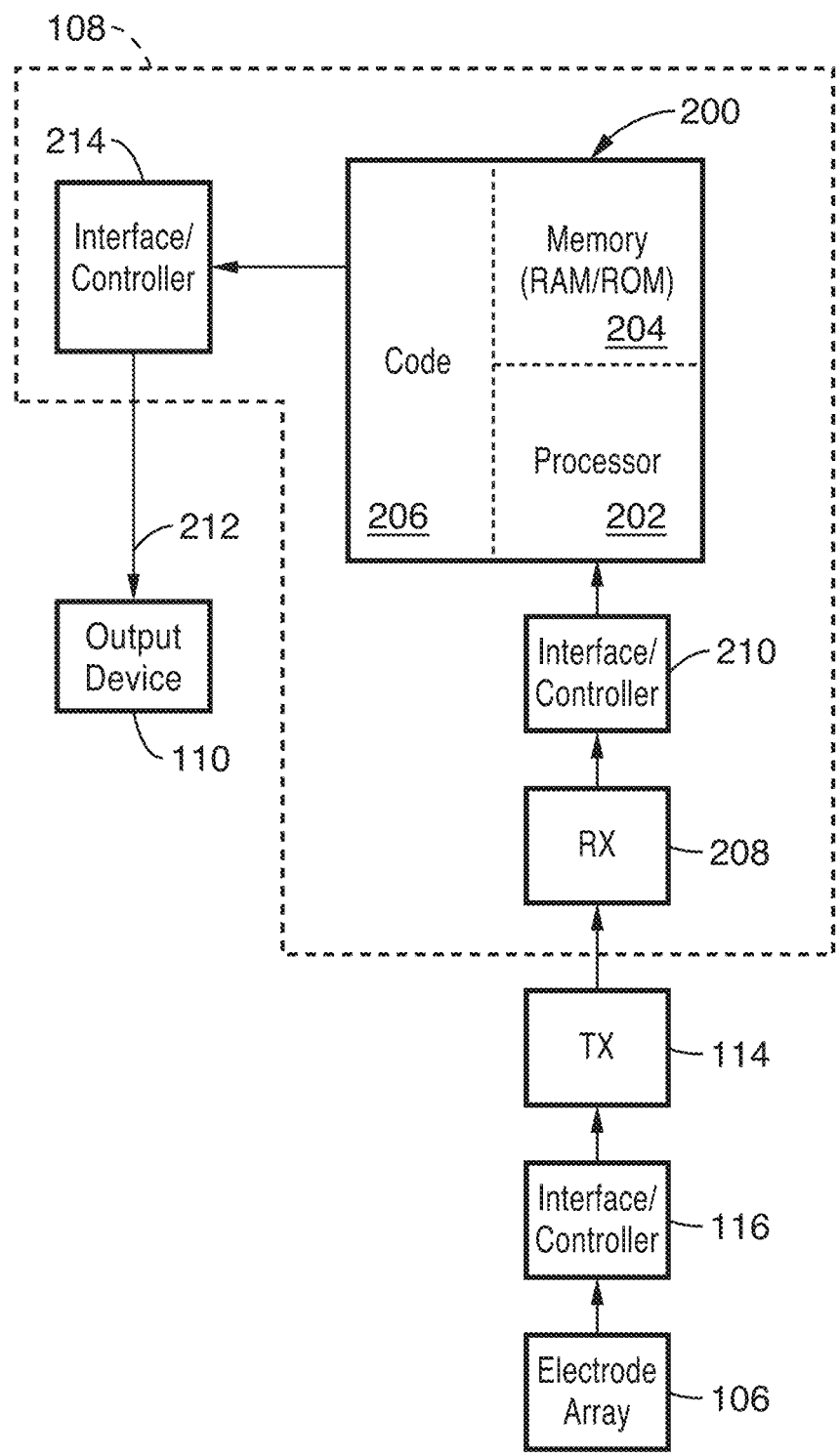

FIG. 2: Functional block diagram showing an embodiment of components of the system of FIG. 1.

Figure 3:
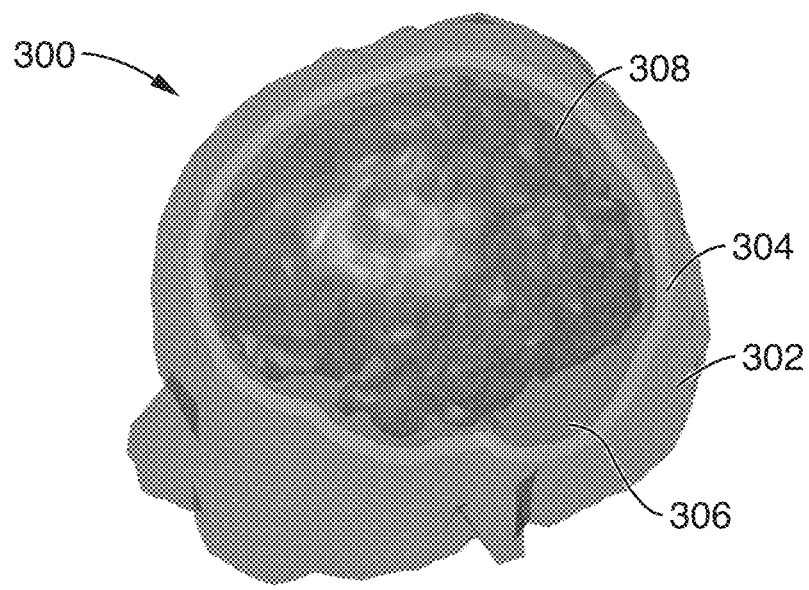

FIG. 3: Realistic head model constructed based on MRI data.

Figure 4:
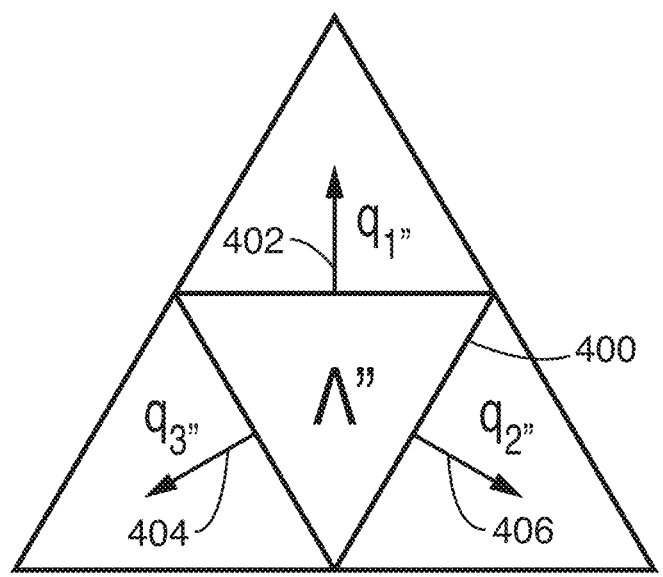

FIG. 4: Illustration of the three normal directions to a triangular voxel.

DETAILED DESCRIPTION

1. Hardware

FIG. 1 and FIG. 2 illustrate the functional components in a generalized embodiment of a brain imaging system according to the technology described herein. It will be appreciated that the embodiment shown may be modified or customized to enable performing the functions described herein.

As illustrated in FIG. 1, the system 100 includes a head-wearable cap 102 that supports a plurality of electrodes 104a through 104n arranged in a high-density array 106, a data acquisition and processing unit 108 that is configured to receive electrical signals from the electrode array and transform the electrical signals into images, and an output device 110 that is configured to display images generated by the data acquisition and processing unit. Optionally, a visual display 112 or other device can be provided to present visual stimulus to a person wearing the cap. When a visual stimulus is presented, electrical signals are captured by the electrode array in response to the visual stimulus, and transformed into images.

Referring more particularly to FIG. 2, the data acquisition and processing unit 108 includes an "engine" 200 having a processor 202, memory 204, and application software code (instructions) 206. The processor 202 can be any suitable conventional processor. The memory 204 may include any suitable conventional RAM type memory and/or ROM type memory with associated storage space for storing the application programming instructions (code) 206.

A conventional wired or wireless communications module 208 (e.g., receiver) may be included as needed for interfacing the electrode array 106 and the data acquisition and processing unit 108. Examples of wireless communication capabilities that can be provided include, but are not limited to, Bluetooth, WiFi, infrared, Ultrawide Band, WiGig, and near field communication. A conventional interface or controller 210 may also be provided if needed. Examples of interfaces or controllers include, but are not limited to, analog to digital converters, digital to analog converters, buffers, etc. The electrical signals from the electrodes can be multiplexed for data acquisition and sampling the signals simultaneously or in any desired grouping or sequence.

In the case of wireless communications between the electrode array 106 and the data acquisition and processing unit 108, a wireless communication module (e.g., transmitter) 114 may be associated with the electrode array. A conventional interface or controller 116 may also be provided if needed. Examples of interfaces or controllers include, but are not limited to, analog to digital converters, digital to analog converters, buffers, microcontroller, and FPGA, etc.

Additionally, the data acquisition and processing unit 108 may include an output 212 to drive one or more output devices. In the preferred embodiment, the output device 110 is a visual display device as illustrated in FIG. 1, but the output device(s) could also include a telemetry or other communications device. A conventional interface or controller 214 may be provided if needed for the output devices. Examples of interfaces or controllers include, but are not limited to, analog to digital converters, digital to analog converters, buffers, etc.

1.1 High-density Electrode Array

The accuracy of a reconstructed brain image can be improved by increasing the number of electrodes, by improving signal-to-noise-ratio (SNR), and by using better inverse algorithms. We have identified several criteria to quantitatively measure the performance of the reconstructed brain image. One criterion is "relative error", which measures the relative sum of square error of the reconstructed image compared to the ground truth. The smaller it is, the higher the reconstruction accuracy. Another criteria is "degree of focalization", which is defined as the ratio between the reconstructed and original energies stored in the original patch area. The larger it is, the higher the spatial resolution. A further criterion is "localization error", which is defined as the distance between the peak of the true source and the reconstructed source. The smaller it is, the higher the localization accuracy. Increasing electrode number and using better inverse methods can improve the accuracy of the reconstructed brain image.

For purposes of this disclosure, we consider an ultra-dense electrode array suitable for fully capturing the functional brain information with high temporal and spatial resolution to be an array with about 64 to 5,000 electrodes for EEG, and about 256 to 10,000 electrodes for ECoG.

1.2 Wireless Technology

In order to conduct ultra dense brain imaging under natural habitual environment, one embodiment of the system integrates wireless technology with the system electronics. It is preferable to transmit neural data up to Gigabits at permissibly low power at the cortex. Accordingly, in embodiment, the system includes an integrated energy efficient wireless transceiver that is capable of supporting wide bandwidth. We have designed two subsystems: (1) an Ultra Wide Band (UWB) transceiver that is able to support approximately 100 megabits; and (2) a Millimeter wave (60 GHz) Gigabit wireless transceiver that is low-power (approximately 10 mW) and the lowest energy per bit (2.08 pJ/b) RF link.

1.3 Data Acquisition

In one embodiment, the system also includes a data acquisition system comprising one or more of the following elements: multi-channel amplifier, filter, multiplexer, analog-to-digital converter, and related components. Additionally, since electronic noise has a large influence on the accuracy of brain imaging, an amplifier with input referred noise as low as 1 uV is preferable. With smaller input referred noise, we are able to capture the signals with higher frequency (800-1000 Hz). In contrast to a conventional EEG system with limited bandwidth (<100 Hz), higher frequency components are highly correlated to cognition tasks, especially in Brain-Machine-Interface (BMI) applications.

1.4 Spatially Focused Electrode Technology

When using an electrode array for high density recordings, every adjacent electrode can record reduplicated signals from its neighborhood. Prior approaches that directly use a dense electrode array for large channel-accounts neural sensing can suffer from high mutual signal occurs in adjacent electrodes due to low spatial resolution. In conventional electrode recording, the recorded signals are mixed together in adjacent electrodes when pitch between electrodes is small. In some instances, this mutual signal effect can become worse as the electrode number increases and electrodes become closer to each other. If the mutual signal effect is an issue, one way to address the issue to use employ a discrete surface Laplacian based electrode array with optimized weighting selection as described in U.S. Patent Application Publication No. US 2016/0192854 A1 published on Jul. 7, 2016, incorporated herein by reference in its entirety, which provides adjustable spatial resolution of each electrode for neural recording (EEG, ECoG, etc.). The result is that signals from out-of-the-electrode area are reduced, and thus the spatial resolution in the forward imaging is greatly improved.

2. Artifact Cancellation

In one embodiment, the system also includes a motion artifact removal scheme. Most conventional systems eliminate motion artifacts in the digital domain, which has several notable drawbacks. For example, the motion artifact is much larger than the signal of interest and may saturate the amplifier of the EEG. If this occurs, the EEG information during that time will be lost and is unrecoverable.

To overcome the problems of the above approach, in one embodiment we subtract the motion artifact in the analog domain by using skin impedance levels as an indication of the motion artifact signal. By simultaneously measuring the skin impedance levels and the EEG signal, we can estimate the motion artifact with an adaptive filter. This approach allows us to cancel out the motion artifact in the analog domain. The system can effectively cancel the noise due to electrode motion in real time and allow for a much more precise recording given the same dynamic range. It is also less computationally demanding, as it does not rely on ICA for subtraction of noise.

3. Realistic Head Model Based on Individual MRI

In order to improve the brain imaging accuracy, we construct a realistic head model for each individual based on his/her own structural MR image. With the well-known Fieldtrip toolbox, we first segment the head into three layers, i.e., scalp, skull and brain, and then construct a triangular mesh for each layer. The cortex surface is also triangulated into a fine mesh with 16384 triangles, each corresponding to a potential dipole source. Then the well-known boundary element method (BEM) is applied to construct the head model and calculate the lead field matrix. FIG. 3 schematically shows a realistic head model 300 containing the scalp 302, skull 304, brain layers 306, and the cortex surface source model 308.

4. Software

Integrated Software can be provided to allow users to operate the system conveniently. For example, the user can use a graphic user interface (GUI) to manipulate the hardware, record and process the signal, and monitor brain dynamics in real-time.

5. Applications

The electrode-based brain imaging system can be used to quantitatively evaluate brain state during social interactions and facilitate the development of the cognitive based computing/interface. Specifically, some applications include, but are not limited to, the following.

5.1 Online Personalized Learning/Training

The imaging system described herein can be applied to facilitate online personalized learning. Current online learning methods are very passive without adaptability. Also current online learning methods do not take advantage of sensory/tracking technology. We envision an optimal online learning system to be a fusion of various new sensory/tracking technologies with a brain state analyzer. With the analyzed real-time brain state, the learning materials can be customized for individuals dynamically and thus optimal personal learning strategy can be devised.

5.2 Brain Disorders

Neurological disorders, such as epilepsy, depression, schizophrenia and Alzheimer's disease, can also be investigated by the disclosed system. With our imaging system, the real-time brain dynamics can be monitored and thus both temporal and spatial causality relationship can be defined, which will be able to help diagnose and treat these brain disorders.

6. Algorithms

The brain contains of billions of neurons, which create local current fields when the neurons are activated. These current fields pass different tissues (e.g. gray matter, cerebrospinal fluid, skull, scalp, etc.) and result in the recorded electrical potential on the scalp as the electroencephalogram (EEG), which is referred to as forward problem. On the other hand, converting the electrical recording back into the brain space in the form of 3D brain image is called inverse problem. It is highly desirable to develop forward and inverse imaging techniques with excellent temporal and spatial resolution.

7. Sparsity and Smoothness Enhanced EEG Brain Imaging

EEG source imaging is able to reconstruct brain images with excellent temporal resolution (~ms) as well as support free body movement, but is limited by the relatively low spatial resolution. To overcome this limitation, many regularization techniques, e.g., $l_1$-norm, total variation (TV) and sparse TV have been proposed, which rely on the assumption that the sources are sparse by themselves or in a transform domain. However, these methods generate either over-focused or nonsmooth results with relatively high localization error.

Accordingly, we have developed what we refer to as a "Sparsity and Smoothness enhanced Method Of Optimized electrical TomograpHy (s-SMOOTH)" to improve the spatial resolution and localization accuracy of reconstructed brain images. Our method aims to enhance the smoothness of brain image and recover the varying intensity of the source distribution, resulting in a brain image with high reconstruction accuracy. By defining a voxel-based Total Generalized Variation (vTGV) regularization on a triangular mesh to enhance high-order smoothness, we improve the localization accuracy. We further utilize $l_{1-2}$ regularization to enhance sparsity of the image thus improving the spatial resolution.

As a first step, we employ the well-known total generalized variation (TGV) regularization, which assumes that the image is piecewise polynomial therefore taking the higher order derivatives into account. It is well known that the $l_1$-norm regularization imposes sparsity in the original source domain, and TV imposes sparsity in the first spatial derivative. The TGV is able to impose sparsity in higher order derivatives along multiple directions. The TGV possesses a great potential in compressive sensing MRI reconstruction and image deconvolution, but, to the best of our knowledge, TGV has not been applied to EEG source imaging as of yet.

Furthermore, since TGV is defined on a 2D image, but the cortex surface is a 3D irregular surface, we have developed a voxel-based TGV (vTGV) regularization which extends the definition of the second order TGV from 2D image to 3D triangular mesh. Additionally, we incorporate the $l_{1-2}$ regularization to further enhance the reconstruction sparsity comparing to the $l_1$-norm regularization.

By applying the alternating direction method of multipliers (ADMM) (also known as split Bregman in the image processing community), we derive an efficient numerical algorithm. A variety of tests on synthetic data with various noise levels and source configurations demonstrated that our approach outperforms the state-of-the-art methods in terms of total reconstruction accuracy, localization accuracy and focalization degree. Tests on P300 data further demonstrated that our method is able to preserve high order smoothness and improve the spatial resolution.

7.1 Methodology 7.1.1 EEG Inverse Problem

As a noninvasive method, electroencephalography (EEG) is used to obtain brain activity and detect abnormalities that may be associated with certain brain disease. In an EEG test, neurons in the brain are activated and local currents are generated, which can travel through different tissues, e.g., gray matter, cerebrospinal fluid (CSF), skull and scalp. These currents result in electrical potentials on the scalp, which are recorded by electrodes as the EEG signals. The EEG inverse problem refers to the process of identifying the distributions of currents in the form of a 3D brain image given the electrical recordings.

To formulate the inverse problem in mathematical expressions, we consider a source model assuming that dipole sources are located on the cortex surface, which is discretized as a mesh consisting of a large number of small triangles. Thereafter, we treat each triangle as one voxel in the discretized source space, and the terms triangle and voxel are used interchangeably. In addition, we assume that the orientation of the dipoles is perpendicular to the cortex surface. Let $b \in \mathbb{R}^N$ be the electrical potential on the scalp measured by the electrodes, where N is the number of electrodes, and $u \in \mathbb{R}^M$ be the neural current density distributed in each dipole location. The electrode potential b can be related to the neural current u by the following linear equation $$b = Au + n, \quad (1)$$

where $A \in \mathbb{R}^{N \times M}$ is called lead field matrix. Note that $A_{i,j}$ denotes the electrical potential measured by the ith electrode due to an unit dipole source at the jth voxel. The matrix A can be calculated by using Maxwell's equations and the properties of the brain. Here $n \in \mathbb{R}^N$ denotes the noise, including background neural noise, electronic noise and electrode noise. Usually the number of voxels M ($\sim 10^4$) is much larger than the number of electrodes N ($\sim 10^2$), thus the linear system of Eq. (1) is highly under-determined and has infinitely many solutions.

The lead field matrix A in Eq. (1) can be computed by constructing a head model. For the synthetic data, we use the head model template provided by Fieldtrip toolbox. For real data, we construct a realistic head model based on the MRI data of the subject using Fieldtrip. We first segment the head into three layers, i.e., scalp, skull and brain, and then construct a triangular mesh for each layer. The cortex surface is also triangulated into a fine mesh with 16384 triangles, each corresponding to a potential dipole source. Then the boundary element method (BEM) is applied to construct the head model and calculate the lead field matrix.

7.1.2 High Order Smoothness for EEG Images

TGV was designed to preserve high order of smoothness in image processing problems. Since the cortex surface has complicated geometries and topological structures, it is important to choose an appropriate regularization tailored to such irregular surface. We discretize the cortex surface to be a 3D triangular mesh and have developed a voxel-based TGV (vTGV) regularization on it to impose high order smoothness.

Firstly, we will briefly review the definition of the second order TGV on a 2D image. Given a 2D image u that is twice continuously differentiable on a bounded set $\tilde{\Omega} \subset \mathbb{R}^2$, the second order TGV of u with the coefficient $\alpha = (\alpha_1, \alpha_2)$ can be defined as the following infimal convolution $$TVG_\alpha^2(u) = \min_{p=(p_1, p_2)} \alpha_1 \|\nabla u - p\|_1 + \alpha_2 \|\tilde{\varepsilon}(p)\|_1, \quad (2)$$

where $\nabla$ is the 2D gradient operator, and the operator $\tilde{\varepsilon}$ is defined by $$\tilde{\varepsilon}(p) = \begin{bmatrix} \frac{\partial p_1}{\partial x} & \frac{1}{2}\left(\frac{\partial p_2}{\partial x} + \frac{\partial p_1}{\partial y}\right) \\ \frac{1}{2}\left(\frac{\partial p_2}{\partial x} + \frac{\partial p_1}{\partial y}\right) & \frac{\partial p_2}{\partial y} \end{bmatrix}. \quad (3)$$

Note that $\|\tilde{\varepsilon}(p)\|_1$ is the sum of all $l_1$-norms of the entries in the matrix $\varepsilon(p)$. Next, we generalize the definition of TGV and define vTGV on a 3D triangular mesh $\Omega$ that consists of a collection of triangular voxels. In order to define the spatial derivatives on triangular mesh, we treat the centroid of each triangular voxel as a dipole. Since each voxel has three voxels connected, three directional derivatives on $\mathbb{R}^3$ can be used to define "gradient" of the density function u. Consider a triangular voxel $\Lambda \in \Omega$, which is homeomorphic to $\mathbb{R}^2$, we assume that $q_1, q_2, q_3$ are three normal directions along three edges for $\Lambda$, where $q_i \in \mathbb{R}^3$ depends on the shape of the triangle $\Lambda$. For instance, FIG. 4 illustrates three normal directions associated with an equilateral triangle 400. The gradient of u restricted on $\Lambda$ is defined by $$\hat{\nabla}u = \begin{bmatrix} \frac{\partial u}{\partial q_1} \\ \frac{\partial u}{\partial q_2} \\ \frac{\partial u}{\partial q_3} \end{bmatrix}, \frac{\partial u}{\partial q_i} = \lim_{\substack{h \to 0 \\ x, x+hq_i \in \Lambda}} \frac{u(x+hq_i) - u(x)}{h}. \quad (4)$$

Note that this definition is in the local sense and it can be considered as an extension of the gradient operator in $\mathbb{R}^2$ into the gradient in a 2D manifold. Given a differentiable function $p=(p_1, p_2, p_3)$, the operator $\varepsilon$ acted on p restricted to $\Lambda$ is defined by $$\varepsilon(p) = \begin{bmatrix} \frac{\partial p_1}{\partial q_1} & \frac{1}{2}\left(\frac{\partial p_2}{\partial q_1} + \frac{\partial p_1}{\partial q_2}\right) & \frac{1}{2}\left(\frac{\partial p_3}{\partial q_1} + \frac{\partial p_1}{\partial q_3}\right) \\ \frac{1}{2}\left(\frac{\partial p_1}{\partial q_2} + \frac{\partial p_2}{\partial q_1}\right) & \frac{\partial p_2}{\partial q_2} & \frac{1}{2}\left(\frac{\partial p_3}{\partial q_2} + \frac{\partial p_2}{\partial q_3}\right) \\ \frac{1}{2}\left(\frac{\partial p_1}{\partial q_3} + \frac{\partial p_3}{\partial q_1}\right) & \frac{1}{2}\left(\frac{\partial p_2}{\partial q_3} + \frac{\partial p_3}{\partial q_2}\right) & \frac{\partial p_3}{\partial q_3} \end{bmatrix}. \quad (5)$$

This operator can be considered as an extension of $\tilde{\varepsilon}$ in Eq. (3), tailored to the 3D triangular mesh $\Omega$.

Next, we discuss the discretization of the operators $\hat{\nabla}$ and $\varepsilon$. On the triangular mesh $\Omega$, we first define the finite difference operator matrix $D \in \mathbb{R}^{3M \times M}$ as follows $$D_{i,j} = \begin{cases} 1, & \text{if } j = l; \\ -1, & \text{if } j \in \{k_{l,1}, k_{l,2}, k_{l,3}\}; \\ 0, & \text{otherwise.} \end{cases} \quad (6)$$

Here $l = \lceil i/3 \rceil \in \{1, \ldots, M\}$ is the lth triangle, where $\lceil \; \rceil$ is the ceiling function, and $k_{l,1}, k_{l,2}, k_{l,3}$ are the indices of the triangles sharing the same edge with the lth triangle. Based on the definition of $\varepsilon$ in Eq. (5), the second order difference operator matrix $E \in \mathbb{R}^{3M \times M}$ is defined as $$E = \frac{1}{2}(\hat{D} + \hat{D}^T), \text{ where } \hat{D} = [D \; D \; D]. \quad (7)$$

Note that $\hat{D}$ can be generated by using the Kronecker product, denoted by $\otimes$, of two matrices $$\hat{D} = I_{1 \times 3} \otimes D, \text{ where } I_{1 \times 3} = [1 \; 1 \; 1]. \quad (8)$$

One can see that $\hat{\nabla}u$ is discretized by Du, and $\varepsilon(p)$ is discretized by Ep. Once the discretization of D and E is available, TV and the second order vTGV with the coefficients $\alpha_1$ and $\alpha_2$ can be defined as $$TV(u) = \|Du\|_1, \quad (9)$$

$$vTGV_{(\alpha_1,\alpha_2)}^2(u) = \min_{p \in \mathbb{R}^{3M}} \alpha_1 \|Du - p\|_1 + \alpha_2 \|Ep\|_1. \quad (10)$$

TV is able to well preserve the edges of piecewise constant images, but to cause staircase effects for natural images. By involving high order derivatives, vTGV generalizes TV and is able to reduce staircase effects by assuming that the image to be reconstructed is piecewise polynomial. In particular, our second order vTGV assumes that the underlying potential is piecewise linear, which implies the sparsity of second spatial derivatives. Although a natural image may have higher order smoothness, it is sufficient to use the second order vTGV in practice, since performance enhancement is limited but more computations are required for higher order vTGV. Therefore, we only use the second order vTGV regularization.

7.1.3 Sparsity of EEG Images

Although the brain contains a substantial amount of neurons, only a small subset is active in most cognitive activities. This suggests that the brain image to be reconstructed contains a lot of zeros or small values and thereby has sparse structure. There are three types of regularizations that can utilize the sparsity property of the signal:

(a) $l_0$-norm type. The $l_0$-norm of $u \in \mathbb{R}^M$ is defined as $$\|u\|_0 = |\{i : u_i \neq 0\}|, \quad (11)$$

i.e., the number of nonzero entries in u.

(b) $l_1$-norm type. The $l_1$-norm of u is defined as $$\|u\|_1 = \Sigma_{i=1}^M |u_i|. \quad (12)$$

Since $l_0$-regularized problem is computational NP-hard, the $l_1$-regularization as a convex relation of $l_0$-norm can be used to reduce numerical complexity. In addition, the convexity of this regularization can guarantee the uniqueness of the minimizer regardless of the initial guess.

(c) $l_{1-2}$ type. Recently, the regularization based on the difference of two convex functions, i.e., $$\|u\|_{1-2,\beta} = \|u\|_1 - \beta \|u\|_2, \quad (13)$$

where $\|u\|_2 = \sqrt{\Sigma_{i=1}^M |u_i|^2}$, $0 < \beta \leq 1$, has shown potential in image processing and compressive sensing reconstruction in terms of sparsity and fast convergence. Note that this $l_{1-2}$ type regularization is not convex whereas the $l_1$ type is convex.

In our approach, we unify the $l_1$ and $l_{1-2}$ type regularizations by allowing $\beta = 0$ in (13), so that the sparsity regularization term could be adjusted by tuning the parameter $\beta$.

7.1.4 EEG Reconstruction Algorithm

We developed the following model to reconstruct the EEG brain image $$\min_u \frac{1}{2} \|Au - b\|_2^2 + vTGV_{(\alpha_1,\alpha_2)}^2(u) + \alpha_3 \|u\|_{1-2,\beta}, \quad (14)$$

where $vTGV_{(\alpha_1,\alpha_2)}^2(u)$ is defined in Eq. (10), and $\|u\|_{1-2,\beta}$ is defined in Eq. (13). The first data fidelity term reflects the statistics of the Gaussian noise. Here $\alpha_i > 0$ are tuning parameters which control the contribution of each regularization term. Note that if $\beta = 0$, the $l_{1-2}$ regularization reduces to the $l_1$ regularization. If we require p=0, then the vTGV regularization reduces to the TV. To solve the problem, an efficient numerical algorithm (Algorithm 1) based on the ADMM is derived below.

7.1.5 EEG Reconstruction Algorithm Derivation

In this section, we derive an efficient numerical algorithm based on ADMM. Since the dual norm of $\|\cdot\|_2$ is itself, i.e., $$\|u\|_2 = \max_{\|q\|_2 \leq 1} \langle u, q \rangle,$$

the model of Eq. (14) can be reformulated as $$\min_{u, \|q\|_2 \leq 1} \frac{1}{2} \|Au - \beta\|_2^2 + \alpha_1 \|Du - p\|_1 + \alpha_2 \|Ep\|_1 + \alpha_3 (\|u\|_1 - \beta \langle u, q \rangle).$$

Next we apply the difference of convex function algorithm (DCA) to obtain the following two subproblems $$\begin{cases} q \leftarrow u/\|u\|_2, \\ (u, p) \leftarrow \underset{u,p}{\operatorname{argmin}} \frac{1}{2}\|Au - b\|_2^2 + \alpha_1\|Du - p\|_1 \\ \qquad\qquad + \alpha_2\|Ep\|_1 + \alpha_3(\|u\|_1 - \langle u, q\rangle). \end{cases} \quad (16)$$

In particular, the second subproblem can be solved efficiently using ADMM. By the change of variables, it can be further written as $$\min_{u,p,x,y,z} \frac{1}{2}\|Au - b\|_2^2 + \alpha_1\|x\|_1 + \alpha_2\|y\|_1 + \alpha_3(\|z\|_1 - \beta\langle z, q\rangle)$$

subject to $x = Du - p$, $y = Ep$, $z = u$.

By introducing the scaled multipliers $\tilde{x}$, $\tilde{y}$, $\tilde{z}$, we have the following augmented Lagrangian function $$\mathcal{L}(u, p, x, y, z, \tilde{x}, \tilde{y}, \tilde{z}) =$$
$$\frac{1}{2}\|Au - b\|_2^2 + \alpha_1\|x\|_1 + \alpha_2\|y\|_1 + \alpha_3(\|z\|_1 - \beta\langle z, q\rangle) +$$
$$\frac{\rho}{2}(\|Du - p - x\|_2^2 + 2\langle Du - p - x, \tilde{x}\rangle + \|Ep - y\|_2^2$$
$$+ 2\langle Ep - y, \tilde{y}\rangle + \|u - z\|_2^2 + 2\langle u - z, \tilde{z}\rangle).$$

Note that this version is equivalent to the standard augmented Lagrangian function up to scaling of multipliers. We group the variables u, p, x, y, z into three blocks, i.e., u, p and (x, y, z). Then the ADMM yields the following algorithm:

$$\begin{cases} u \leftarrow \underset{u}{\operatorname{argmin}}\, \mathcal{L}(u, p, x, y, z, \tilde{x}, \tilde{y}, \tilde{z}) \\ p \leftarrow \underset{p}{\operatorname{argmin}}\, \mathcal{L}(u, p, x, y, z, \tilde{x}, \tilde{y}, \tilde{z}) \\ (x, y, z) \leftarrow \underset{x,y,z}{\operatorname{argmin}}\, \mathcal{L}(u, p, x, y, z, \tilde{x}, \tilde{y}, \tilde{z}) \\ \tilde{x} \leftarrow \tilde{x} + Du - p - x \\ \tilde{y} \leftarrow \tilde{y} + Ep - y \\ \tilde{z} \leftarrow \tilde{z} + u - z + \frac{\alpha_3 \beta}{\rho}q \end{cases} \quad (17)$$

Moreover, u and p can be solved explicitly as follows:

$$\begin{cases} u = (A^T A + \rho(D^T D + I))^{-1}(A^T b + \rho D^T(p + x - \tilde{x}) + \rho(z - \tilde{z})) \\ p = (E^T E + I)^{-1}((Du - x + \tilde{x}) + E^T(y - \tilde{y})). \end{cases}$$

In addition, due to the separability of variables, the (x, y, z)-subproblem boils down to three independent subproblems with respect to x, y and z, respectively, each of which has a closed-form solution represented by proximal operators. For example, the z-subproblem can be solved by using the proximal operator of $l_1$-norm $$\underset{z}{\operatorname{argmin}}\left\{\alpha_3\|z\|_1 + \frac{\rho}{2}\left\|u - z + \tilde{z} + \frac{\alpha_3 \beta}{\rho}q\right\|^2\right\} = \quad (18)$$
$$prox_{\alpha_3/\rho}\left(u + \tilde{z} + \frac{\alpha_3 \beta}{\rho}q\right),$$

where $prox_\gamma(x) = sign(x) \odot max\{|x| - \gamma, 0\}$ with component-wise multiplication $\odot$, also known as shrinkage operator.

Combining DCA for the problem of Eq. (16) and ADMM for the (u,p)-subproblem, we obtain the algorithm summarized in Algorithm 1:

---
Algorithm 1 s-SMOOTH EEG Reconstruction
---

Input the electrical measurements b, the sensing matrix A, the difference operators D and E, the parameters $\alpha_1$, $\alpha_2$, $\alpha_3$, $\rho$ and $\beta$, as well as the stopping criteria of the algorithm.
Initialize the current density u and the auxiliary variables p, x, y, z, $\tilde{x}$, $\tilde{y}$, $\tilde{z}$ as zero vectors.
Iterate the algorithm to update the above variables as follows $$\begin{cases} u \leftarrow (A^T A + \rho(D^T D + I))^{-1}(A^T b + \rho D^T(p + x - \tilde{x}) + \rho(z - \tilde{z})) \\ p \leftarrow (E^T E + I)^{-1}((Du - x + \tilde{x}) + E^T(y - \tilde{y})). \\ x \leftarrow prox_{\alpha_1/\rho}(Du - p + \tilde{x}) \\ y \leftarrow prox_{\alpha_2/\rho}(Ep + \tilde{y}) \\ z \leftarrow prox_{\alpha_3/\rho}\left(u + \tilde{z} + \frac{\alpha_3 \beta}{\rho}q\right) \\ \tilde{x} \leftarrow \tilde{x} + Du - p - x \\ \tilde{y} \leftarrow \tilde{y} + Ep - y \\ \tilde{z} \leftarrow \tilde{z} + u - z + \frac{\alpha_3 \beta}{\rho}q \end{cases}$$

End when the stopping criteria are met.
Output the reconstructed current density u.

---

Note that in this example the entire matrix A is scaled by multiplying $10^5$ in order to reduce round-off errors. Algorithm 1 terminates when either the maximal number of iterations or the minimal relative change is reached. In our experiments, the iteration is halted after 1000 iterations or the relative change of u is smaller than $10^{-3}$. Here the relative change of u is defined as $$u_{change} = \frac{\|u_{new} - u_{old}\|_2}{\|u_{old}\|_2}.$$

In general, ADMM is simple to implement with linear convergence even if part of the objective function is non-differentiable. Our empirical experience shows that the $l_{1-2}$ regularization further promotes faster convergence of the algorithm than its $l_1$-regularized counterpart.

7.2 Results

In this section, we evaluate the performance of the method by conducting experiments on various synthetic data sets and two real data sets.

7.2.1 Simulation Protocols

In our simulation, the source is synthesized using the Gaussian-tapered patch. First, a source center is seeded on the cortex surface, then its neighbors are gradually recruited to make a patch. Because of properties of the Gaussian function, the source intensity reaches a peak at the center and gradually decreases to zero as it moves away from the center. To make a comprehensive comparison, we tested a variety of sources with different sizes. Specifically, we used the sources containing 50, 100, 200 and 300 triangular voxels, which corresponds to 1.0 cm, 1.4 cm, 1.9 cm, 2.2 cm in radius. After the source patch was generated, independent and identically distributed (i.i.d.) background neural noise was added to each voxel. In addition, i.i.d. electrode and electronic noise were added to each channel. For the sake of simplicity, we assumed that all the noise, including background neural noise, electrode noise, and electronic noise, were all additive white Gaussian noise. As a criterion widely used to measure the noise level, signal-to-noise ratio (SNR) is defined as $$SNR = 10 \log_{10} \frac{P_{signal}}{P_{noise}},$$

where $P_{signal}$ and $P_{noise}$ are the power of the signal and the noise, respectively. In our testing, we used SNR varying from 5 dB to 30 dB. In our simulation, a SNR of 10 dB was assumed by default. Finally, the synthetic signal was normalized to make sure that the amplitude of the signal falls into the range from 10 µV to 100 µV, which is the typical EEG signal amplitude of an adult human.

7.2.2 Quantitative Metric for Accuracy Measurement

For the synthetic data, we evaluated the performance of an EEG image reconstruction method using the following criteria:

(a) Relative square error (SE), which measures the relative difference between the reconstructed source and the true one. The smaller the SE is, the higher accuracy the reconstructed image will have. SE is defined as $$SE = \frac{\|\hat{u} - u\|_2}{\|u\|_2}$$

where u is the ground truth, û is the reconstructed source.

(b) Localization error (LE), which measures the distance between the peaks of the true source and the reconstructed one. Suppose that there are k underlying sources, and $LE_k$ is the localization error of the kth source, then LE is defined as the average localization error of all the k sources. Let $d_{ki}$ be the distance between the ith voxel to the peak of the kth true source, and $I_k$ be a set of the voxel indices that are closest to the kth source peak, then LE can be expressed as $$LE = \frac{1}{K} \sum_k LE_k, \quad LE_k = \left\{ d_{ki} \mid i = \arg\min_{i' \in I_k} \|u_{i'}\|_2 \right\}.$$

(c) Degree of focalization (DF), which describes how focal the reconstructed source is, and is defined as $$DF = \frac{\|\hat{u}_S\|_2^2}{\|u_S\|_2^2},$$

where $u_S$ is u restricted on the original patch area S which is a subset of the whole source space Ω. The higher the DF is, the higher the spatial resolution the reconstructed image will have.

To summarize, the criterion SE reflects the total reconstruction accuracy, LE reflects the localization accuracy, and DF represents focalization degree and spatial resolution of the reconstructed source.

7.2.3 Parameter Selection

Parameter selection is very important to the performance of various EEG reconstruction methods. In our algorithm, the parameters $\alpha_1$, $\alpha_2$, $\alpha_3$ are selected to make a balance between smoothness and sparseness. Based on our large amount of experiments, the optimal parameter selection does not change significantly as the source size changes.

Thus, we fix these parameters for the same noise level. For different noise levels, we fix the ratio of all parameters, and adjust the scale factor according to the noise level. Usually, when the noise level decreases, more weights should be distributed to the data fidelity term, which requires that the regularization parameters $\alpha_1$, $\alpha_2$, $\alpha_3$ to be smaller.

For the synthetic data sets with SNR between 5 dB and 30 dB, we set $\alpha_1$ between 10~70. For simplicity, we set $\alpha_2$ to be equal to $\alpha_1$. For $\alpha_3$, we find that the performance of the proposed method is not sensitive to $\alpha_3$ as long as it is in the range of $\alpha_3 = 0.1 \sim 0.5 \alpha_1$. Usually, we tune $\alpha_1$ first, then $\alpha_2$, $\alpha_3$. In Algorithm 1, the parameter ρ controls the convergence speed of the algorithm, which is set to $10\alpha_1$ by default.

7.2.4 Synthetic Data Results

For synthetic data, we tested the s-SMOOTH method against four representative source localization methods in the literature: MNE, sLORETA, FOCUSS and TV-$l_1$. Since different criteria may favor different parameters, in order to make comparison fair, we chose the optimal parameters for those methods mainly based on the first criterion SE. Testing two synthetic data sets of single source and three sources, respectively, we found that for MNE and sLORETA which are based on the Tikhonov regularization ($l_2$-norm), the reconstructed sources were spread out and had relatively low spatial resolution. Therefore, it was difficult for them to identify the number and the extent of the sources when multiple sources exist. Regarding FOCUSS, which is based on the $l_0$-norm regularization, the spatial resolution was greatly improved. However, the reconstructed source was over-focused and it failed to recover the extent of the sources. The TV-$l_1$ method recovered the number and the extent of sources, and was also able to separate several sources which are close to each other. However, since the reconstructed source was piecewise constant, it had difficulty localizing the peak of the sources. Compared to the TV-based method and its variants, we found that our method provides a smoother result, which reflects the current intensity variation with high accuracy.

To further compare the robustness of all the aforementioned methods, we systematically tested multiple sources with various noise levels as well as various source sizes. For better visualization, we normalized all the results by dividing them by the total power and then displayed them in the same color axis. We evaluated the results of different methods under the SNR of 5 dB, 10 dB, 20 dB, 30 dB. By comparing the results with the ground truth, we found that as the SNR gets higher, the reconstruction accuracy is improved for all the methods. It is important to point out that our method outperforms other methods even when the noise level is increased. We also evaluated the results for various source sizes. In four data sets, the sources contained three patches of the same size, where each patch was made up of 50, 100, 200 and 300 voxels, respectively. In a fifth data set, we evaluated a case of mixed source sizes, where three sources had different numbers of voxels. We found that our method provided the smallest error to the ground truth for each source configuration.

In summary, our method has shown consistently superior performance over all other methods in recovering the extent and preserving current density variation of the sources regardless of noise level and source size.

In addition, we performed quantitative evaluations to further compare our method and other competing methods. We evaluated the results of the three quantitative criteria defined above under various noise levels, where the source size was fixed as 300 voxels. In order to avoid inconsistency due to different noise configurations, we repeated the experiment 50 times by adding random noise and displaying the averaged result in the plots. From an SE plot, we found that our method had the smallest relative square error. Due to the over-focused effect, FOCUSS had the worst performance in terms of relative square error and hence it yields low reconstruction accuracy. Our method had the smallest localization error among all methods because of the enhanced smoothness of the reconstructed image. Compared to our method, the TV-$l_1$ method had relatively large localization error since it attempted to produce a piecewise constant image and thereby had difficulty locating the peak of each source. From a DF plot, all the methods with the $l_0/l_1$-norm regularization or the $l_{1-2}$ regularization, i.e., FOCUSS, TV-$l_1$, and s-SMOOTH, produced results of high degree of focalization.

We performed a quantitative evaluation with source sizes 50, 100, 200, 300 voxels. Here the SNR was fixed to be 10 dB. From an SE plot, we found that our method has small relative square errors, and hence has high reconstruction accuracy. As the source size increases, SE decreases in our method whereas it increases for most of other methods, which implies that our method has the great advantage of dealing with large sources. In an LE plot, we found that the localization error for our method remained relatively low regardless of the source size; however, other methods generate larger localization error when source is larger. Furthermore, a DF plot showed that our method has large focalization degree for different sources. Overall, our method showed outstanding performance in terms of all criteria. In particular, as the source size increases, it shows consistent good performance whereas other methods produce worse results.

7.2.5 Real Data Results

We also applied our method to P300 source localization. It has been widely accepted that the P300 is likely to be generated by multiple distributed sources. A consistent pattern of P300 sources has been shown by various techniques, such as intracranial recordings, lesion studies and fMRI-EEG combination, that the target-related responses locate in the parietal cortex and the cingulate, with stimulus specific sources in the superior temporal cortex for the auditory stimulation and in the inferior temporal and superior parietal cortex for the visual stimulation.

In our EEG experiment, two event-related potential (ERP) data sets were collected from a normal subject with a 64-channel EEG device (ANT Neuro, Enschede Netherlands). The first data set was auditory stimulation, where two audio signals of 1500 Hz (target, 40 trials) and 1000 Hz frequency (nontarget, 160 trials) were presented to the subject. The eyes of the subject were closed during auditory stimulation. The second data set was visual stimulation. Two different pictures were presented to the subject, where the target was a picture of a fierce shark (40 trials) and the nontarget was picture of an old man (160 trials). The eyes of the subject were open during visual stimulation. The subject was asked to focus on the target stimuli and count the number when receiving the target stimuli. The EEG data was sampled at 512 Hz, filtered by a band pass filter of 0.5-30 Hz, and referenced to the average of all channels. In the end, the average was taken across the trials in order to improve the SNR, and the difference between the target and nontarget was used to do source localization.

The realistic head model was constructed based on the high resolution structural MRI (General Electric, Waukesha, Wis., USA) of the subject using Fieldtrip toolbox. In the model, the head was first segmented into three compartments: scalp, skull, and brain. Those compartments were then triangulated into meshes. The source model (cortex surface) was generated by Freesurfer that yields a triangular mesh with >100000 vertices, which was then downsampled by MNE Suite to 16384 triangles. Finally, the lead field matrix was calculated using BEM method in FieldTrip.

We compared our method with sLORETA, which is known to have high localization accuracy and has been widely used to localize the sources of P300. We evaluated the P300 source localization results of auditory stimulation at the peak (312 ms), and found that both sLORETA and our method were able to detect sources from parietal cortex and superior temporal cortex. The sources on the occipital cortex can be interpreted by the alpha wave due to the closed eyes. Compared to sLORETA, our method greatly improves the spatial resolution and produces a smoother result. We also evaluated the results of visual stimulation at the peak (398 ms), in which the sources in posterior temporal, parietal, and mesial frontal cortices are found. Our method showed the ability to produce brain images of much higher order smoothness and spatial resolution compared to sLORETA.

Note that there were only 64 electrodes in this data, and therefore the spatial resolution of the reconstructed brain images was relatively limited. With an increased number of electrodes, the spatial resolution and localization accuracy will further be improved.

7.3 Conclusion

We have described an EEG inverse method Sparsity and Smoothness enhanced Method Of Optimized electrical TomograpHy (s-SMOOTH), which combines the vTGV and the $l_{1-2}$ regularizations to improve both high spatial resolution and localization accuracy for EEG source imaging. Considering the complicated geometries of the cortex surface, we defined a vTGV regularization on a 3D triangular mesh expressed as an infimal convolution form. The vTGV regularization enhances the high order smoothness and thus is able to improve localization accuracy, while the $l_{1-2}$ regularization enhances the sparsity of the brain images. Note that some related methods, e.g., TV and TV-$l_1$, can be considered as the special cases of our method by choosing proper parameters. A large number of experiments on synthetic and real data sets showed that our s-SMOOTH is able to improve spatial resolution and recover the extent of the sources. Our method also consistently outperforms over other competitive methods in terms of the following quantitative criteria: relative square error (SE), localization error (LE), and degree of focalization (DF). The tests on two P300 data sets from a normal subject further showed the great advantage of s-SMOOTH over sLORETA in terms of brain image quality.

While this disclosure focuses on EEG source imaging, it will be appreciated that our method is equivalently applicable to MEG source imaging. It will be appreciated that the parameter selection step could be done in a more automatic fashion by treating the parameters as unknown variables in our model of Eq. 14 and then solving the corresponding optimization problem using techniques such as the bi-level approach.

8. Graph Fractional-Order Total Variation EEG Source Reconstruction

EEG source imaging is able to reconstruct sources on the brain from scalp measurements with high temporal resolution. Due to the limited number of sensors, it is very challenging to locate the source accurately with high spatial resolution. Recently, several total variation (TV) based methods have been proposed to explore sparsity of the source spatial gradients, which is based on the assumption that the source is constant at each subregion. However, since the sources have more complex structures in practice, these methods have difficulty in recovering the current density variation and locating source peaks.

To overcome this limitation, we developed a graph Fractional-Order Total Variation (gFOTV) based method, which provides the freedom to choose the smoothness order by imposing sparsity of the spatial fractional derivatives so that it locates source peaks accurately. We refer to this method as "graph fractional-order total variation EEG source reconstruction".

FOTV can be used to solve image processing problems. Unlike TV which imposes sparsity of first-order spatial derivatives, FOTV can choose a more elegant smoothness order for the underlying source by imposing sparsity of $\alpha$-order derivatives ($\alpha>0$). Therefore, our method is capable of reconstructing the brain image with higher-order smoothness and preserving natural intensity changes of the brain image. As a consequence, the localization accuracy of peaks is greatly improved compared to TV-based methods.

In order to extend the traditional FOTV defined on a 2D rectangular grid to an irregular cortical surface, we define a graph FOTV (gFOTV) on a triangular mesh using shortest paths on a graph. In fact, TV-based methods can be considered as a special case in our framework when $\alpha=1$. In addition, we derive an efficient algorithm using the alternating direction method of multipliers (ADMM).

8.1 Graph Fractional-Order Total Variation

Fractional-order TV is used in image processing to enhance smoothness with relatively low computational cost. In this section, we focus on the anisotropic version so that the objective function of the derived minimization problem is separable.

The anisotropic fractional-order TV in a 2D rectangular mesh is defined as follows:

$$TV_\alpha(u) = \|\nabla^\alpha u\|_1 = \sum_{i,j=1}^{N} \left( |(D_x^\alpha u)_{i,j}| + |(D_y^\alpha u)_{i,j}| \right)$$

where $\alpha \in (1,2)$. Here the fractional derivative is based on the Gruwald-Letnikov derivative definition $$(D_x^\alpha u)_{i,j} = \sum_{k=0}^{K} w_\alpha(k) u(i-k, j), \quad (D_y^\alpha u)_{i,j} = \sum_{k=0}^{K} w_\alpha(k) u(i, j-k),$$

where the coefficients are $$w_\alpha(k) = (-1)^k \frac{\Gamma(\alpha+1)}{k!\Gamma(\alpha-k+1)}.$$

It is easy to see that $w_\alpha(0)=1$ and $w_\alpha(1)=-\alpha$. Moreover, if $\alpha=1$, then $TV_\alpha$ is the traditional TV. If $\alpha=2$, $D_x^\alpha/D_y^\alpha$ approximates the second partial derivative of u along the x/y-direction. Although the above definition is also valid for $\alpha \in (0,1) \cup (2,\infty)$, researchers have been found that $\alpha \in (1,2)$ achieves the best performance in applications.

Since the cortex surface is an irregular 3D surface consisting of gyms and sulcus, we define a graph $\alpha$-order TV with $\alpha \in [1,2]$ tailored to such surface. After discretizing the cortex surface, we create a graph whose nodes correspond to the centroids of all triangles. For a specific node $v_i$, let $d(v_i, v_j)$ be the number of nodes on the shortest path connecting the nodes $v_i$ and $v_j$, which is in or close to a geodesic of the underlying surface passing through $v_i$ and $v_j$. Given a path $p=(v_{i-m_0}, v_{m_1}, \ldots, v_{m_K})$ where the shortest distance between the nodes $v_{m_0}$ and $v_{m_j}$ is j nodes, the fractional-order derivative along the path p is defined as $$(D_p^\alpha u)_i := D_p^\alpha u(v_i) = \sum_{v \in p} w_\alpha(d(v_0, v))u(v) = \sum_{j=0}^{K} w_\alpha(j) u(v_{m_j}).$$

Then the discretized fractional-order TV of u is defined as follows:

$$TV_\alpha(u) = \|D_\alpha u\|_1 = \sum_{i=1}^{N} \sum_{p \in P(i;K)} |(D_p^\alpha u)_i|,$$

where $P(i;K)$ is the set of all paths starting from the ith node with length K nodes.

The shortest path between each node pair can be calculated by the breadth-first search (BFS) algorithm. For a specific node $v_i$, the nodes at level k, i.e., the nodes have shortest distance k from $v_i$, are assigned the weight $w_\alpha(k)$. In particular, if $\alpha=1$, then $D_\alpha$ is exactly the finite difference operator used in the TV-based methods. If $\alpha=2$, then $w_\alpha(2)=1$ and $w_\alpha(k)=0$ for $k>2$ which implies that all nodes at level more than two are assigned zero weight. If $\alpha \in (1,2)$, then the weights $w_\alpha(k)$ will gradually decay as the shortest distance k goes to infinity. As the value of a increases from 1 to 2, the decay rate of weights $w_\alpha(k)$ becomes larger. Note that K specifies the maximal level of nodes to be used. Due to the sparse structure of the underlying u, it is sufficient to choose $K \leq 4$ levels of neighboring nodes to achieve the desired accuracy in our experiments.

8.2 Model and Algorithm

After defining FOTV on triangular mesh of cortex surface, we use the following fractional-order TV regularized EEG source reconstruction model to improve high order smoothness of the brain image $$\min_u \left\{ \frac{1}{2} \|Au - b\|_2^2 + \lambda TV_\alpha(u) \right\}$$

where $\lambda>0$ is regularization parameter, which controls the tradeoff between the data fidelity term and the sparsity term. By change of variables, the above problem can be converted to a linear equality constrained minimization problem $$\min_{u,v} \left\{ \frac{1}{2} \|Au - b\|_2^2 + \lambda \|v\|_1 \right\} \text{ subject to } D_\alpha u = v.$$

Then the ADMM yields the following algorithm (Algorithm 2):

---

Algorithm 2 gFOTV EEG Reconstruction

Input the electrical measurements b, the sensing matrix A, the fractional-order derivative operator $D_\alpha$, the parameters $\lambda$, $\rho$ and $\gamma$, as well as the stopping criteria of the algorithm.
Initialize the current density u and the auxiliary variables v and $\tilde{v}$ as zero vectors.

-continued

Algorithm 2 gFOTV EEG Reconstruction

Iterate the algorithm to update the above variables as follows $$\begin{cases} v = \text{shrink}(D_\alpha u + \tilde{v}, \lambda/\rho) \\ u = \arg\min_u \left\{ \frac{1}{2}\|Au - b\|_2^2 + \frac{\rho}{2}\|D_\alpha u - v + \tilde{v}\|_2^2 \right\} \\ \quad = (A^T A + \rho D_\alpha^T D_\alpha)^{-1}(A^T b + \rho D_\alpha^T(v - \tilde{v})) \\ \tilde{v} \leftarrow \tilde{v} + \gamma(D_\alpha u - v) \end{cases}$$

End when the stopping criteria are met.
Output the reconstructed current density u.

Here the parameters $\rho>0$, $\gamma \in (0,(\sqrt{5}+1)/2)$ and the shrinkage operator is defined componentwise $\text{shrink}(u,\mu)_i = \text{sign}(u_i)\max\{|u_i|-\mu,0\}$.

8.3 Simulation and Results
8.3.1 Simulation Protocol

In our simulation, Gaussian patches were used to simulate sources in the brain. To represent sources at different locations, we randomly selected three sources located at different lobes of the cortex surface. In addition, to evaluate the performance of the method for different source sizes, we simulated sources containing 50, 100, 150, 200, 250 voxels, corresponding to 1.0 cm, 1.4 cm, 1.7 cm, 1.9 cm, 2.1 cm in radius, respectively.

After the sources were generated, we added random independent and identically distributed (i.i.d.) Gaussian noise to each voxel as background neural noise. Additionally, we added the electrode and electronic noise to each channel. For the signal-to-noise ratio (SNR), we used 10 dB by default. As for the electrode number, we chose 346 to make sure that there are enough electrodes and the performance of the EEG source localization method was not limited by the electrode number. Finally, the signal was normalized to fall between 10 μV to 100 μV, which is a typical range of amplitude for an adult EEG signal.

8.3.2 Quantitative Criteria

We used the following three quantitative criteria to evaluate performance of each reconstruction method from different aspects.

(a) Total reconstruction error (TRE), aiming to calculate the total reconstruction accuracy. It measures the relative error between the reconstructed source and the true one, and it is defined as $\text{TRE} = \|\hat{u}-u\|_2/\|u\|_2$, where $u$ and $\hat{u}$ are the ground truth and the reconstructed source respectively.

(b) Localization error (LE), aiming at evaluating the localization accuracy.

It measures the averaged localization error between the peaks of the true and reconstructed sources, and it can be expressed as $\text{LE} = \Sigma_k \text{LE}_k/K$, $\text{LE}_k = \{d_{ki} | i = \arg\min_{i \in I_k} \|u_i\|_2\}$, where $d_{ki}$ is the distance between the ith voxel to the peak of the kth true source, and $I_k$ is a set of the voxel indices that are closest to the kth source peak.

(c) Degree of focalization (DF) is used to evaluate spatial resolution, which measures how focal the reconstructed source is. It is defined as $\text{DF} = \|\hat{u}_S\|_2^2/\|u_S\|_2^2$, where us is u restricted on the original patch area S.

8.3.3 Parameter Selection

In the operator $D_\alpha$, the parameter $\alpha$ specifies the order of the spatial derivative domain where we want to impose sparsity constraint on. As $\alpha$ becomes larger, we impose sparsity of higher order derivatives, and therefore the reconstructed sources become smoother and decay faster. When $\alpha=1$, the source decay speed is the slowest, which is the case of TV that the current density is piecewise constant. In our experience, it works well when $\alpha=2$. By choosing a to be a fraction between 1 and 2, all level nodes will be assigned a non-zero weight, which enhances reconstruction smoothness. Specifically, $\alpha=1.6$ is appropriate for all our experiments. In addition, the spatial resolution will be higher than that of $\alpha=2$. In Algorithm 2, the regularization parameter $\lambda$ controls the balance between the data fidelity term and the sparsity term. When the source size becomes larger, $\lambda$ should be tuned to be a little larger. As the noise level becomes higher, $\lambda$ needs to be a little smaller. According to our experience, it works pretty well by simply choosing $\lambda$ around 1. The parameter $\rho$ affects the convergence speed of Algorithm 2, and is set as $10\lambda$ by default. Finally, the parameter $\gamma$ is fixed as 1.

8.3.4 Simulation Results

First, we evaluated the performance of the method using $\alpha=2$ and $\alpha=1.6$, as compared with several state-of-the-art methods: sLORETA, $l_1$-norm based and TV-based methods. From our evaluation of the reconstruction results of three sources at different locations of the cortex surface, we found that the spatial resolution of sLORETA was very low, since it is based on the Tikhonov regularization using $l_2$-norm. The $l_1$-norm based method greatly improved the spatial resolution because it imposes sparsity of the source in itself, but it yields over-focused reconstructed sources and fails to identify the spatial extent of the sources. The TV-based method showed good performance in identifying the spatial extent and preserving edges. However, it did not recover the varying intensity of the source, because of the assumption that the source intensity is piecewise constant.

In contrast, our method generated the reconstructed images closest to the ground truth. It not only provided high spatial resolution, but also successfully reconstructed the intensity variation and the spatial extent of the sources. It is also worth noting that $\alpha=1.6$ is able to further enhance the spatial resolution compared to $\alpha=2$.

We further evaluated our method quantitatively by using various quantitative criteria defined above. To show the robustness and consistency, we conducted a large number of simulation tests with different source sizes, and averaged results of 50 realizations with different noise configurations. From the TRE curve we could see that our method provided the smallest total reconstruction error. We note that the TV-based method also showed a relatively small total reconstruction error compared to other methods. From the LE curve, our method showed the smallest localization error, since it makes the brain image smoother by imposing sparsity in higher order derivative instead of the first order derivative. Since sLORETA can provide high localization accuracy, sLORETA also showed small localization error. The TV-based method, however, produced relatively large localization error, which is because the reconstructed sources are constant in each subregion therefore cannot pinpoint the peak of the source accurately. Finally, the DF curve showed that all of the methods with sparsity constraints exhibit high focalization degree. It is interesting to note that for gFOTV-based methods, $\alpha=1.6$ further enhanced the spatial resolution. Compared to other methods, the spatial resolution of sLORETA was the lowest, as indicated by its name "standardized low resolution brain electromagnetic tomography".

To summarize, our method demonstrated superior performance from all the criteria including total reconstruction accuracy, localization accuracy and spatial resolution.

8.4 Conclusion

As can be seen, we have developed an efficient and accurate EEG source reconstruction method by defining a novel graph fractional-order total variation (gFOTV) adapted for a triangular mesh of the cortical surface. This method imposes sparsity in $\alpha$-order spatial derivatives with $\alpha \in [1,2]$, which includes the TV-based methods as a special case when $\alpha=1$. By tuning the parameter $\alpha$, the method provides the freedom to choose a more elegant order of smoothness for the underlying brain image. Therefore, it not only provides high spatial resolution, but also recovers the current density variation and localizes the source peaks with high accuracy. In addition, the algorithm is parameter friendly and is not sensitive to the parameter selection. A variety of simulation experiments demonstrated that the method consistently outperforms the state-of-the-art methods both qualitatively and quantitatively. Note also that our current framework could be extended by using spatially variant smoothness orders for different subregions in an automatic way to further reduce the reconstruction error.

Compared to other approaches, the electrode-based brain imaging system described herein may provide several beneficial features, which include but are not limited to, the following:

(1) provides an ultra-dense electrode array covering either portion or an entire head;

(2) is electrical field based for measuring the brain activity directly;

(3) has the capability of studying the correlation between the neural activity and behavior, and thus the brain dynamics;

(4) has excellent temporal resolution thus can capture neural activities at the scale of approximately ms;

(5) supports natural habitual environment and free moving subjects with a wireless transceiver;

(6) data acquisition system with input referred noise as low as 1 uV that is able to record higher frequency signal;

(7) has focused electrode technology for adaptive spatial filtering and SNR restoration;

(8) uses a realistic head model based on high-resolution MRI from the subject;

(9) employs a brain imaging algorithm based on "compressed sensing" technique to achieve high spatial resolution comparable to fMRI;

(10) is light weight, low energy, and low cost implementation;

(11) the ability to reconstruct the brain image with high spatial resolution;

(12) the ability to identify spatial extent of the sources;

(13) the ability to recover the source intensity variation and localize peak of the sources accurately;

(14) freedom to impose sparsity in $\alpha$-order ($\alpha>0$, including fraction) spatial derivative of the sources, thus providing brain image with high-order smoothness;

(15) is user-friendly that only one parameter needs to be tuned;

(16) has low computational requirements;

(17) has efficient optimization using alternating direction method of multipliers (ADMM).

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

From the description herein, it will be appreciated that the present disclosure encompasses multiple embodiments which include, but are not limited to, the following:

1. An electrode-based brain imaging system, said system comprising: (a) an ultra-high density electrode array; (b) a data acquisition and processing unit; and (c) an output device; (d) the data acquisition and processing unit comprising: (i) a computer processor; and (ii) a memory storing instructions executable by the computer processor; (iii) wherein when executed by the computer processor, said instructions transform electrical signals acquired by said data acquisition and processing unit from said electrode array into a three-dimensional image by performing s-SMOOTH based reconstruction and presenting said image to said output device.

2. The system of any preceding embodiment, wherein said s-SMOOTH based reconstruction comprises: (1) defining a voxel-based total generalized variation (vTGV) on triangular mesh to enhance the smoothness of the reconstructed source; (2) incorporating $l_{1-2}$ regularization to enhance the sparsity of reconstructed source; (3) performing voxel-based total generalized variation (vTGV) and $l_{1-2}$ regularized EEG source reconstruction according to $$\min_u \frac{1}{2} \| Au - b \|_2^2 + vTGV^2_{(\alpha_1, \alpha_2)}(u) + \alpha_3 \| u \|_{1-2,\beta}$$

where the first term is data fidelity term, the second term is vTGV regularization, and the third term is $l_{1-2}$ regularization; and (4) using alternating direction method of multipliers (ADMM) according to:

---
Algorithm 1 s-SMOOTH EEG Reconstruction
---
Input the electrical measurements b, the sensing matrix A, the difference operators D and E, the parameters $\alpha_1$, $\alpha_2$, $\alpha_3$, $\rho$ and $\beta$, as well as the stopping criteria of the algorithm.
Initialize the current density u and the auxiliary variables p, x, y, z, x̃, ỹ, z̃ as zero vectors.
Iterate the algorithm to update the above variables as follows $$\begin{cases} u \leftarrow (A^T A + \rho(D^T D + I))^{-1}(A^T b + \rho D^T (p + x - \tilde{x}) + \rho(z - \tilde{z})) \\ p \leftarrow (E^T E + I)^{-1}((Du - x + \tilde{x}) + E^T(y - \tilde{y})). \\ x \leftarrow \text{prox}_{\alpha_1/\rho}(Du - p + \tilde{x}) \\ y \leftarrow \text{prox}_{\alpha_2/\rho}(Ep + \tilde{y}) \\ z \leftarrow \text{prox}_{\alpha_3/\rho}\left(u + \tilde{z} + \frac{\alpha_3 \beta}{\rho} q\right) \\ \tilde{x} \leftarrow \tilde{x} + Du - p - x \\ \tilde{y} \leftarrow \tilde{y} + Ep - y \\ \tilde{z} \leftarrow \tilde{z} + u - z + \frac{\alpha_3 \beta}{\rho} q \end{cases}$$

where $\text{prox}_\gamma(x) = \text{sign}(x) \odot \max\{|x| - \gamma, 0\}$ with componentwise multiplication $\odot$, also known as shrinkage operator.
End when the stopping criteria are met.
Output the reconstructed current density u.

---

3. The system of any preceding embodiment, wherein said instructions when executed by the computer processor remove artifacts from the electrical signals by performing steps comprising: subtracting motion artifacts in the analog domain, by using skin impedance levels as an indication of the motion artifact signal; and estimating motion artifacts with an adaptive filter by simultaneously measuring skin impedance levels and the electrical signals; wherein motion artifacts are canceled in the analog domain.

4. The system of any preceding embodiment, wherein the output device comprises a visual display device.

5. The system of any preceding embodiment, wherein together the ultra-high density electrode array and data acquisition and processing unit are configured for capturing functional brain information with high temporal and spatial resolution.

6. The system of any preceding embodiment, wherein the ultra-high density electrode array comprises from about 64 to about 10,000 electrodes.

7. The system of any preceding embodiment, further comprising a wireless communications interface interconnecting the electrode array and the data acquisition and processing unit.

8. The system of any preceding embodiment, wherein said data acquisition and processing unit has a low noise input configured for acquiring said electrical signals and routing said signals to said computer processor.

9. The system of any preceding embodiment, wherein said ultra-high density electrode array is developed using a realistic head model constructed based on high-resolution MRI from a subject.

10. The system of any preceding embodiment, wherein said instructions when executed by said computer processor carry out a spatially focused electrode algorithm which reduces cross-talking among electrodes and improves the spatial resolution in the forward imaging by applying an optimal weighting matrix.

11. An electrode-based brain imaging system, said system comprising: (a) an ultra-high density electrode array; (b) a data acquisition and processing unit; (c) a wireless communications interface interconnecting the electrode array and the data acquisition and processing unit; and (d) a visual display device; (e) the data acquisition and processing unit comprising: (i) a computer processor; and (ii) a memory storing instructions executable by the computer processor; (iii) wherein when executed by the computer processor, said instructions transform electrical signals acquired by said data acquisition and processing unit from said electrode array into a three-dimensional image by performing s-SMOOTH based reconstruction and presenting said image to said visual display device; and (iv) wherein said s-SMOOTH based reconstruction comprises: (1) defining a voxel-based total generalized variation (vTGV) on triangular mesh to enhance the smoothness of the reconstructed source; (2) incorporating $l_{1-2}$ regularization to enhance the sparsity of reconstructed source; (3) performing voxel-based total generalized variation (vTGV) and $l_{1-2}$ regularized EEG source reconstruction according to $$\min_u \frac{1}{2} \| Au - b \|_2^2 + vTGV^2_{(\alpha_1, \alpha_2)}(u) + \alpha_3 \| u \|_{1-2,\beta}$$

where the first term is data fidelity term, the second term is vTGV regularization, and the third term is $l_{1-2}$ regularization; and (4) using alternating direction method of multipliers (ADMM) according to:

---
Algorithm 1 s-SMOOTH EEG Reconstruction
---
Input the electrical measurements b, the sensing matrix A, the difference operators D and E, the parameters $\alpha_1$, $\alpha_2$, $\alpha_3$, $\rho$ and $\beta$, as well as the stopping criteria of the algorithm.
Initialize the current density u and the auxiliary variables p, x, y, z, x̃, ỹ, z̃ as zero vectors.

-continued

Algorithm 1 s-SMOOTH EEG Reconstruction

Iterate the algorithm to update the above variables as follows $$\begin{cases} u \leftarrow (A^T A + \rho(D^T D + I))^{-1}(A^T b + \rho D^T(p + x - \tilde{x}) + \rho(z - \tilde{z})) \\ p \leftarrow (E^T E + I)^{-1}((Du - x + \tilde{x}) + E^T(y - \tilde{y})) \\ x \leftarrow \text{prox}_{\alpha_1/\rho}(Du - p + \tilde{x}) \\ y \leftarrow \text{prox}_{\alpha_2/\rho}(Ep + \tilde{y}) \\ z \leftarrow \text{prox}_{\alpha_3/\rho}\left(u + \tilde{z} + \frac{\alpha_3 \beta}{\rho} q\right) \\ \tilde{x} \leftarrow \tilde{x} + Du - p - x \\ \tilde{y} \leftarrow \tilde{y} + Ep - y \\ \tilde{z} \leftarrow \tilde{z} + u - z + \frac{\alpha_3 \beta}{\rho} q \end{cases}$$

where $\text{prox}_\gamma(x) = \text{sign}(x) \odot \max\{|x| - \gamma, 0\}$ with componentwise multiplication $\odot$, also known as shrinkage operator.
End when the stopping criteria are met.
Output the reconstructed current density u.

12. An electrode-based brain imaging system, said system comprising: (a) an ultra-high density electrode array; (b) a data acquisition and processing unit; and (c) an output device; (d) the data acquisition and processing unit comprising: (i) a computer processor; and (ii) a memory storing instructions executable by the computer processor; (iii) wherein when executed by the computer processor, said instructions transform electrical signals acquired by said data acquisition and processing unit from said electrode array into a three-dimensional image by performing graph Fractional-Order Total Variation (gFOTV) based reconstruction and presenting said image to said output device.

13. The system of any preceding embodiment, wherein said graph Fractional-Order Total Variation (gFOTV) based reconstruction comprises:

Algorithm 2 gFOTV EEG Reconstruction

Input the electrical measurements b, the sensing matrix A, the fractional-order derivative operator $D_\alpha$, the parameters $\lambda$, $\rho$ and $\gamma$, as well as the stopping criteria of the algorithm.
Initialize the current density u and the auxiliary variables v and $\tilde{v}$ as zero vectors.
Iterate the algorithm to update the above variables as follows $$\begin{cases} v = \text{shrink}(D_\alpha u + \tilde{v}, \lambda/\rho) \\ u = \arg\min_u \left\{\frac{1}{2}\|Au - b\|_2^2 + \frac{\rho}{2}\|D_\alpha u - v + \tilde{v}\|_2^2\right\} \\ \quad = (A^T A + \rho D_\alpha^T D_\alpha)^{-1}(A^T b + \rho D_\alpha^T(v - \tilde{v})) \\ \tilde{v} \leftarrow \tilde{v} + \gamma(D_\alpha u - v) \end{cases}$$

End when the stopping criteria are met.
Output the reconstructed current density u.

where the parameters $\rho > 0$, $\gamma \in (0, (\sqrt{5}+1)/2)$ and the shrinkage operator is defined componentwise $\text{shrink}(u, \mu)_i = \text{sign}(u_i) \max\{|u_i| - \mu, 0\}$, b=the electrical measurements, A=the sensing matrix, and $D_\alpha$ the fractional order derivative operator.

14. The system of any preceding embodiment, wherein said graph Fractional-Order Total Variation (gFOTV) based reconstruction comprises: defining fractional-order total variation on a triangular mesh by treating the mesh as a graph and using shortest path searching to obtain different layers of neighbors; and performing fractional-order total variation (FOTV) regularized EEG source reconstruction and using alternating direction method of multipliers (ADMM) according to:

$$\min_{u,v}\left\{\frac{1}{2}\|Au - b\|_2^2 + \lambda\|v\|_1\right\} \text{ subject to } D_\alpha u = v$$

$$\begin{cases} v = \text{shrink}(D_\alpha u + \tilde{v}, \lambda/\rho) \\ u = \arg\min_u \left\{\frac{1}{2}\|Au - b\|_2^2 + \frac{\rho}{2}\|D_\alpha u - v + \tilde{v}\|_2^2\right\} \\ \quad = (A^T A + \rho D_\alpha^T D_\alpha)^{-1}(A^T b + \rho D_\alpha^T(v - \tilde{v})) \\ \tilde{v} \leftarrow \tilde{v} + \gamma(D_\alpha u - v) \end{cases}$$

where the parameters $\rho > 0$, $\gamma \in (0, (\sqrt{5}+1)/2)$ and the shrinkage operator is defined componentwise $\text{shrink}(u, \mu)_i = \text{sign}(u_i) \max\{|u_i| - \mu, 0\}$, b=the electrical measurements, A=the sensing matrix, and $D_\alpha$ the fractional order derivative operator.

15. The system of any preceding embodiment, wherein said instructions when executed by the computer processor remove artifacts from the electrical signals by performing steps comprising: subtracting motion artifacts in the analog domain, by using skin impedance levels as an indication of the motion artifact signal; and estimating motion artifacts with an adaptive filter by simultaneously measuring skin impedance levels and the electrical signals; wherein motion artifacts are canceled in the analog domain.

16. The system of any preceding embodiment, wherein the output device comprises a visual display device.

17. The system of any preceding embodiment, wherein together the ultra-high density electrode array and data acquisition and processing unit are configured for capturing functional brain information with high temporal and spatial resolution.

18. The system of any preceding embodiment, wherein said electrode array comprises from about 64 to about 10,000 electrodes.

19. The system of any preceding embodiment, further comprising a wireless communications interface interconnecting the electrode array and the data acquisition and processing unit.

20. The system of any preceding embodiment, wherein said data acquisition and processing unit has a low noise input configured for acquiring said electrical signals and routing said signals to said computer processor.

21. The system of any preceding embodiment, wherein said ultra-high density electrode array is developed using a realistic head model constructed based on high-resolution MRI from a subject.

22. The system of any preceding embodiment, wherein said instructions when executed by said computer processor carry out a spatially focused electrode algorithm which reduces cross-talking among electrodes and improves the spatial resolution in the forward imaging by applying an optimal weighting matrix.

23. An electrode-based brain imaging system, said system comprising: (a) an ultra-high density electrode array; (b) a data acquisition and processing unit; (c) a wireless communications interface interconnecting the electrode array and the data acquisition and processing unit; and (d) a visual display device; (e) the data acquisition and processing unit comprising: (i) a computer processor; and (ii) a memory storing instructions executable by the computer processor; (iii) wherein when executed by the computer processor, said instructions transform electrical signals acquired by said data acquisition and processing unit from said electrode array into a three-dimensional image by performing graph Fractional-Order Total Variation (gFOTV) based reconstruction and presenting said image to said visual display device; and (iv) wherein said graph Fractional-Order Total Variation (gFOTV) based reconstruction comprises: (1) defining fractional-order total variation on a triangular mesh by treating the mesh as a graph and using shortest path searching to obtain different layers of neighbors; and (2) performing fractional-order total variation (FOTV) regularized EEG source reconstruction and using alternating direction method of multipliers (ADMM) according to:

$$\min_{u,v}\left\{\frac{1}{2}\|Au-b\|_2^2+\lambda\|v\|_1\right\} \text{ subject to } D_\alpha u=v$$

$$\begin{cases} v = \text{shrink}(D_\alpha u + \tilde{v}, \lambda/\rho) \\ u = \arg\min_u\left\{\frac{1}{2}\|Au-b\|_2^2 + \frac{\rho}{2}\|D_\alpha u - v + \tilde{v}\|_2^2\right\} \\ \quad = (A^T A + \rho D_\alpha^T D_\alpha)^{-1}(A^T b + \rho D_\alpha^T (v - \tilde{v})) \\ \tilde{v} \leftarrow \tilde{v} + \gamma(D_\alpha u - v) \end{cases}$$

where the parameters $\rho>0$, $\gamma\in(0,(\sqrt{5}+1)/2)$ and the shrinkage operator is defined componentwise $\text{shrink}(u,\mu)_i=\text{sign}(u_i)\max\{|u_i|-\mu,0\}$, b=the electrical measurements, A=the sensing matrix, and $D_\alpha$ the fractional order derivative operator.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An electrode-based brain imaging system, said system comprising:
   (a) an ultra-high density electrode array;
   (b) a data acquisition and processing unit; and
   (c) an output device;
   (d) the data acquisition and processing unit comprising:
      (i) a computer processor; and
      (ii) a memory storing instructions executable by the computer processor;
      (iii) wherein when executed by the computer processor, said instructions transform electrical signals acquired by said data acquisition and processing unit from said electrode array into a three-dimensional image by performing s-SMOOTH based reconstruction and presenting said image to said output device; and
      (iv) wherein said s-SMOOTH based reconstruction comprises:
         (1) defining a voxel-based total generalized variation (vTGV) on triangular mesh to enhance the smoothness of the reconstructed source;
         (2) incorporating $l_{1-2}$ regularization to enhance the sparsity of reconstructed source;
         (3) performing voxel-based total generalized variation (vTGV) and $l_{1-2}$ regularized EEG source reconstruction according to $$\min_u \frac{1}{2}\|Au-b\|_2^2 + vTGV^2_{(\alpha_1,\alpha_2)}(u) + \alpha_3\|u\|_{1-2,\beta}$$

where the first term is data fidelity term, the second term is vTGV regularization, and the third term is $l_{1-2}$ regularization; and
         (4) using alternating direction method of multipliers (ADMM) according to:

---

Algorithm 1 s-SMOOTH EEG Reconstruction

Input the electrical measurements b, the sensing matrix A, the difference operators D and E, the parameters $\alpha_1$, $\alpha_2$, $\alpha_3$, $\rho$ and $\beta$, as well as the stopping criteria of the algorithm.
Initialize the current density u and the auxiliary variables p, x, y, z, $\tilde{x}$, $\tilde{y}$, $\tilde{z}$ as zero vectors.
Iterate the algorithm to update the above variables as follows $$\begin{cases} u \leftarrow (A^T A + \rho(D^T D + I))^{-1}(A^T b + \rho D^T(p+x-\tilde{x}) + \rho(z-\tilde{z})) \\ p \leftarrow (E^T E + I)^{-1}((Du-x+\tilde{x}) + E^T(y-\tilde{y})) \\ x \leftarrow \text{prox}_{\alpha_1/\rho}(Du-p+\tilde{x}) \\ y \leftarrow \text{prox}_{\alpha_2/\rho}(Ep+\tilde{y}) \\ z \leftarrow \text{prox}_{\alpha_3/\rho}\left(u+\tilde{z}+\frac{\alpha_3\beta}{\rho}q\right) \\ \tilde{x} \leftarrow \tilde{x} + Du - p - x \\ \tilde{y} \leftarrow \tilde{y} + Ep - y \\ \tilde{z} \leftarrow \tilde{z} + u - z + \frac{\alpha_3\beta}{\rho}q \end{cases}$$

where $\text{prox}_\gamma(x) = \text{sign}(x) \odot \max\{|x|-\gamma, 0\}$ with componentwise multiplication $\odot$, also known as shrinkage operator.
End when the stopping criteria are met.
Output the reconstructed current density u.

---

2. The system of claim 1, wherein said instructions when executed by the computer processor remove artifacts from the electrical signals by performing steps comprising:
   subtracting motion artifacts in the analog domain, by using skin impedance levels as an indication of the motion artifact signal; and
   estimating motion artifacts with an adaptive filter by simultaneously measuring skin impedance levels and the electrical signals;
   wherein motion artifacts are canceled in the analog domain.

3. The system of claim 1, wherein the output device comprises a visual display device.

4. The system of claim 1, wherein together the ultra-high density electrode array and data acquisition and processing unit are configured for capturing functional brain information with high temporal and spatial resolution.

5. The system of claim 1, wherein the ultra-high density electrode array comprises from about 64 to about 10,000 electrodes.

6. The system of claim 1, further comprising a wireless communications interface interconnecting the electrode array and the data acquisition and processing unit.

7. The system of claim 1, wherein said data acquisition and processing unit has a low noise input configured for acquiring said electrical signals and routing said signals to said computer processor.

8. The system of claim 1, wherein said ultra-high density electrode array is developed using a realistic head model constructed based on high-resolution MRI from a subject.

9. The system of claim 1, wherein said instructions when executed by said computer processor carry out a spatially focused electrode algorithm which reduces cross-talking among electrodes and improves the spatial resolution in the forward imaging by applying an optimal weighting matrix.

10. An electrode-based brain imaging system, said system comprising:
    (a) an ultra-high density electrode array;
    (b) a data acquisition and processing unit;
    (c) a wireless communications interface interconnecting the electrode array and the data acquisition and processing unit; and
    (d) a visual display device;
    (e) the data acquisition and processing unit comprising:
        (i) a computer processor; and
        (ii) a memory storing instructions executable by the computer processor;
        (iii) wherein when executed by the computer processor, said instructions transform electrical signals acquired by said data acquisition and processing unit from said electrode array into a three-dimensional image by performing s-SMOOTH based reconstruction and presenting said image to said visual display device; and
        (iv) wherein said s-SMOOTH based reconstruction comprises:
            (1) defining a voxel-based total generalized variation (vTGV) on triangular mesh to enhance the smoothness of the reconstructed source;
            (2) incorporating $l_{1-2}$ regularization to enhance the sparsity of reconstructed source;
            (3) performing voxel-based total generalized variation (vTGV) and $l_{1-2}$ regularized EEG source reconstruction according to $$\min_u \frac{1}{2}\|Au - b\|_2^2 + vTGV_{(\alpha_1,\alpha_2)}^2(u) + \alpha_3 \|u\|_{1-2,\beta}$$

where the first term is data fidelity term, the second term is vTGV regularization, and the third term is $l_{1-2}$ regularization; and (4) using alternating direction method of multipliers (ADMM) according to:

---
Algorithm 1 s-SMOOTH EEG Reconstruction
---
Input the electrical measurements b, the sensing matrix A, the difference operators D and E, the parameters $\alpha_1$, $\alpha_2$, $\alpha_3$, $\rho$ and $\beta$, as well as the stopping criteria of the algorithm.
Initialize the current density u and the auxiliary variables p, x, y, z, $\tilde{x}$, $\tilde{y}$, $\tilde{z}$ as zero vectors.

---
Algorithm 1 s-SMOOTH EEG Reconstruction
---
Iterate the algorithm to update the above variables as follows $$\begin{cases} u \leftarrow (A^TA + \rho(D^TD + I))^{-1}(A^Tb + \rho D^T(p + x - \tilde{x}) + \rho(z - \tilde{z})) \\ p \leftarrow (E^TE + I)^{-1}((Du - x + \tilde{x}) + E^T(y - \tilde{y})). \\ x \leftarrow \text{prox}_{\alpha_1/\rho}(Du - p + \tilde{x}) \\ y \leftarrow \text{prox}_{\alpha_2/\rho}(Ep + \tilde{y}) \\ z \leftarrow \text{prox}_{\alpha_3/\rho}\left(u + \tilde{z} + \frac{\alpha_3\beta}{\rho}q\right) \\ \tilde{x} \leftarrow \tilde{x} + Du - p - x \\ \tilde{y} \leftarrow \tilde{y} + Ep - y \\ \tilde{z} \leftarrow \tilde{z} + u - z + \frac{\alpha_3\beta}{\rho}q \end{cases}$$

where $\text{prox}_\gamma(x) = \text{sign}(x) \odot \max\{|x| - \gamma, 0\}$ with componentwise multiplication $\odot$, also known as shrinkage operator.
End when the stopping criteria are met.
Output the reconstructed current density u.

11. An electrode-based brain imaging system, said system comprising:
    (a) an ultra-high density electrode array;
    (b) a data acquisition and processing unit; and
    (c) an output device;
    (d) the data acquisition and processing unit comprising:
        (i) a computer processor; and
        (ii) a memory storing instructions executable by the computer processor;
        (iii) wherein when executed by the computer processor, said instructions transform electrical signals acquired by said data acquisition and processing unit from said electrode array into a three-dimensional image by performing graph Fractional-Order Total Variation (gFOTV) based reconstruction and presenting said image to said output device:
        (iv) wherein said graph Fractional-Order Total Variation (gFOTV) based reconstruction comprises:

---
Algorithm 2 gFOTV EEG Reconstruction
---
Input the electrical measurements b, the sensing matrix A, the fractional-order derivative operator $D_\alpha$, the parameters $\lambda$, $\rho$ and $\gamma$, as well as the stopping criteria of the algorithm.
Initialize the current density u and the auxiliary variables v and $\tilde{v}$ as zero vectors.
Iterate the algorithm to update the above variables as follows $$\begin{cases} v = \text{shrink}(D_\alpha u + \tilde{v}, \lambda/\rho) \\ u = \arg\min_u \left\{\frac{1}{2}\|Au - b\|_2^2 + \frac{\rho}{2}\|D_\alpha u - v + \tilde{v}\|_2^2\right\} \\ \quad = (A^TA + \rho D_\alpha^T D_\alpha)^{-1}(A^Tb + \rho D_\alpha^T(v - \tilde{v})) \\ \tilde{v} \leftarrow \tilde{v} + \gamma(D_\alpha u - v) \end{cases}$$

End when the stopping criteria are met.
Output the reconstructed current density u.

where the parameters $\rho > 0$, $\gamma \in (0, (\sqrt{5}+1)/2)$ and the shrinkage operator is defined componentwise $\text{shrink}(u,\mu)_i = \text{sign}(u_i) \max\{|u_i| - \mu, 0\}$, b=the electrical measurements, A=the sensing matrix, and $D_\alpha$ the fractional order derivative operator.

12. The system of claim 11, wherein said graph Fractional-Order Total Variation (gFOTV) based reconstruction comprises:

defining fractional-order total variation on a triangular mesh by treating the mesh as a graph and using shortest path searching to obtain different layers of neighbors; and performing fractional-order total variation (FOTV) regularized EEG source reconstruction and using alternating direction method of multipliers (ADMM) according to:

$$\min_{u,v}\left\{\frac{1}{2}\|Au-b\|_2^2+\lambda\|v\|_1\right\} \text{ subject to } D_\alpha u = v$$

$$\begin{cases} v = \text{shrink}(D_\alpha u + \tilde{v}, \lambda/\rho) \\ u = \arg\min_u\left\{\frac{1}{2}\|Au-b\|_2^2+\frac{\rho}{2}\|D_\alpha u - v + \tilde{v}\|_2^2\right\} \\ \quad = (A^T A + \rho D_\alpha^T D_\alpha)^{-1}(A^T b + \rho D_\alpha^T(v-\tilde{v})) \\ \tilde{v} \leftarrow \tilde{v} + \gamma(D_\alpha u - v) \end{cases}$$

where the parameters $\rho>0$, $\gamma\in(0,(\sqrt{5}+1)/2)$ and the shrinkage operator is defined componentwise $\text{shrink}(u,\mu)_i=\text{sign}(u_i)\max\{|u_i|-\mu,0\}$, b=the electrical measurements, A=the sensing matrix, and $D_\alpha$ the fractional order derivative operator.

13. The system of claim 11, wherein said instructions when executed by the computer processor remove artifacts from the electrical signals by performing steps comprising:
subtracting motion artifacts in the analog domain, by using skin impedance levels as an indication of the motion artifact signal; and
estimating motion artifacts with an adaptive filter by simultaneously measuring skin impedance levels and the electrical signals;
wherein motion artifacts are canceled in the analog domain.

14. The system of claim 11, wherein the output device comprises a visual display device.

15. The system of claim 11, wherein together the ultra-high density electrode array and data acquisition and processing unit are configured for capturing functional brain information with high temporal and spatial resolution.

16. The system of claim 11, wherein said electrode array comprises from about 64 to about 10,000 electrodes.

17. The system of claim 11, further comprising a wireless communications interface interconnecting the electrode array and the data acquisition and processing unit.

18. The system of claim 11, wherein said data acquisition and processing unit has a low noise input configured for acquiring said electrical signals and routing said signals to said computer processor.

19. The system of claim 11, wherein said ultra-high density electrode array is developed using a realistic head model constructed based on high-resolution MRI from a subject.

20. The system of claim 11, wherein said instructions when executed by said computer processor carry out a spatially focused electrode algorithm which reduces cross-talking among electrodes and improves the spatial resolution in the forward imaging by applying an optimal weighting matrix.

21. An electrode-based brain imaging system, said system comprising:
(a) an ultra-high density electrode array;
(b) a data acquisition and processing unit;
(c) a wireless communications interface interconnecting the electrode array and the data acquisition and processing unit; and
(d) a visual display device;
(e) the data acquisition and processing unit comprising:
(i) a computer processor; and
(ii) a memory storing instructions executable by the computer processor;
(iii) wherein when executed by the computer processor, said instructions transform electrical signals acquired by said data acquisition and processing unit from said electrode array into a three-dimensional image by performing graph Fractional-Order Total Variation (gFOTV) based reconstruction and presenting said image to said visual display device; and
(iv) wherein said graph Fractional-Order Total Variation (gFOTV) based reconstruction comprises:
(1) defining fractional-order total variation on a triangular mesh by treating the mesh as a graph and using shortest path searching to obtain different layers of neighbors; and
(2) performing fractional-order total variation (FOTV) regularized EEG source reconstruction and using alternating direction method of multipliers (ADMM) according to:

$$\min_{u,v}\left\{\frac{1}{2}\|Au-b\|_2^2+\lambda\|v\|_1\right\} \text{ subject to } D_\alpha u = v$$

$$\begin{cases} v = \text{shrink}(D_\alpha u + \tilde{v}, \lambda/\rho) \\ u = \arg\min_u\left\{\frac{1}{2}\|Au-b\|_2^2+\frac{\rho}{2}\|D_\alpha u - v + \tilde{v}\|_2^2\right\} \\ \quad = (A^T A + \rho D_\alpha^T D_\alpha)^{-1}(A^T b + \rho D_\alpha^T(v-\tilde{v})) \\ \tilde{v} \leftarrow \tilde{v} + \gamma(D_\alpha u - v) \end{cases}$$

where the parameters $\rho>0$, $\gamma\in(0,(\sqrt{5}+1)/2)$ and the shrinkage operator is defined componentwise $\text{shrink}(u,\mu)_i=\text{sign}(u_i)\max\{|u_i|-\mu,0\}$, b=the electrical measurements, A=the sensing matrix, and $D_\alpha$ the fractional order derivative operator.

22. An electrode-based brain imaging system, said system comprising:
(a) an ultra-high density electrode array;
(b) a data acquisition and processing unit; and
(c) an output device;
(d) the data acquisition and processing unit comprising:
(i) a computer processor; and
(ii) a memory storing instructions executable by the computer processor;
(iii) wherein when executed by the computer processor, said instructions transform electrical signals acquired by said data acquisition and processing unit from said electrode array into a three-dimensional image by performing s-SMOOTH based reconstruction and presenting said image to said output device; and
(iv) wherein said instructions when executed by said computer processor carry out a spatially focused electrode algorithm which reduces cross-talking among electrodes and improves the spatial resolution in the forward imaging by applying an optimal weighting matrix.

23. The system of claim 22, wherein said instructions when executed by the computer processor remove artifacts from the electrical signals by performing steps comprising:
subtracting motion artifacts in the analog domain, by using skin impedance levels as an indication of the motion artifact signal; and estimating motion artifacts with an adaptive filter by simultaneously measuring skin impedance levels and the electrical signals;

wherein motion artifacts are canceled in the analog domain.

24. The system of claim 22, wherein the output device comprises a visual display device.

25. The system of claim 22, wherein together the ultra-high density electrode array and data acquisition and processing unit are configured for capturing functional brain information with high temporal and spatial resolution.

26. The system of claim 22, wherein the ultra-high density electrode array comprises from about 64 to about 10,000 electrodes.

27. The system of claim 22, further comprising a wireless communications interface interconnecting the electrode array and the data acquisition and processing unit.

28. The system of claim 22, wherein said data acquisition and processing unit has a low noise input configured for acquiring said electrical signals and routing said signals to said computer processor.

29. The system of claim 22, wherein said ultra-high density electrode array is developed using a realistic head model constructed based on high-resolution MRI from a subject.

30. An electrode-based brain imaging system, said system comprising:
  (a) an ultra-high density electrode array;
  (b) a data acquisition and processing unit; and
  (c) an output device;
  (d) the data acquisition and processing unit comprising:
    (i) a computer processor; and
    (ii) a memory storing instructions executable by the computer processor;
    (iii) wherein when executed by the computer processor, said instructions transform electrical signals acquired by said data acquisition and processing unit from said electrode array into a three-dimensional image by performing graph Fractional-Order Total Variation (gFOTV) based reconstruction and presenting said image to said output device; and
    (iv) wherein said instructions when executed by said computer processor carry out a spatially focused electrode algorithm which reduces cross-talking among electrodes and improves the spatial resolution in the forward imaging by applying an optimal weighting matrix.

31. The system of claim 30, wherein said graph Fractional-Order Total Variation (gFOTV) based reconstruction comprises:
  defining fractional-order total variation on a triangular mesh by treating the mesh as a graph and using shortest path searching to obtain different layers of neighbors; and
  performing fractional-order total variation (FOTV) regularized EEG source reconstruction and using alternating direction method of multipliers (ADMM) according to:

$$\min_{u,v}\left\{\frac{1}{2}\|Au-b\|_2^2 + \lambda\|v\|_1\right\} \text{ subject to } D_\alpha u = v$$

$$\begin{cases} v = \text{shrink}(D_\alpha u + \tilde{v}, \lambda/\rho) \\ u = \text{argmin}_u\left\{\frac{1}{2}\|Au-b\|_2^2 + \frac{\rho}{2}\|D_\alpha u - v + \tilde{v}\|_2^2\right\} \\ \quad = (A^T A + \rho D_\alpha^T D_\alpha)^{-1}(A^T b + \rho D_\alpha^T(v - \tilde{v})) \\ \tilde{v} \leftarrow \tilde{v} + \gamma(D_\alpha u - v) \end{cases}$$

where the parameters $\rho > 0$, $\gamma \in (0, (\sqrt{5}+1)/2)$ and the shrinkage operator is defined componentwise $\text{shrink}(u,\mu)_i = \text{sign}(u_i) \max\{|u_i|-\mu, 0\}$, b=the electrical measurements, A=the sensing matrix, and $D_\alpha$ the fractional order derivative operator.

32. The system of claim 30, wherein said instructions when executed by the computer processor remove artifacts from the electrical signals by performing steps comprising:
  subtracting motion artifacts in the analog domain, by using skin impedance levels as an indication of the motion artifact signal; and
  estimating motion artifacts with an adaptive filter by simultaneously measuring skin impedance levels and the electrical signals;
  wherein motion artifacts are canceled in the analog domain.

33. The system of claim 30, wherein the output device comprises a visual display device.

34. The system of claim 30, wherein together the ultra-high density electrode array and data acquisition and processing unit are configured for capturing functional brain information with high temporal and spatial resolution.

35. The system of claim 30, wherein said electrode array comprises from about 64 to about 10,000 electrodes.

36. The system of claim 30, further comprising a wireless communications interface interconnecting the electrode array and the data acquisition and processing unit.

37. The system of claim 30, wherein said data acquisition and processing unit has a low noise input configured for acquiring said electrical signals and routing said signals to said computer processor.

38. The system of claim 30, wherein said ultra-high density electrode array is developed using a realistic head model constructed based on high-resolution MRI from a subject.

* * * * *